US008633288B2

(12) United States Patent
Dams et al.

(10) Patent No.: US 8,633,288 B2
(45) Date of Patent: Jan. 21, 2014

(54) FLUORINATED ETHER COMPOUNDS AND METHODS OF USING THE SAME

(75) Inventors: Rudolf J. Dams, Antwerp (BE); Michael S. Terrazas, Prescott, WI (US); Klaus Hintzer, Kastl (DE); Zai-Ming Qiu, Woodbury, MN (US); Miguel A. Guerra, Woodbury, MN (US); Andreas R. Maurer, Langenneufnach (DE); Harald Kaspar, Burgkirchen (DE); Kai H. Lochhaas, Neuoetting (DE); Michael Juergens, Neuoetting (DE); Tilman C. Zipplies, Burghausen (DE); Werner Schwertfeger, Langgons (DE)

(73) Assignee: 3M Innovative Properties Company, St. Paul, MN (US)

( * ) Notice: Subject to any disclaimer, the term of this patent is extended or adjusted under 35 U.S.C. 154(b) by 201 days.

(21) Appl. No.: 13/054,601

(22) PCT Filed: Jul. 15, 2009

(86) PCT No.: PCT/US2009/050627
§ 371 (c)(1),
(2), (4) Date: Jan. 18, 2011

(87) PCT Pub. No.: WO2010/009191
PCT Pub. Date: Jan. 21, 2010

(65) Prior Publication Data
US 2011/0124782 A1    May 26, 2011

Related U.S. Application Data

(60) Provisional application No. 61/081,942, filed on Jul. 18, 2008.

(51) Int. Cl.
*C08F 4/44* (2006.01)

(52) U.S. Cl.
USPC ............. 526/144; 424/9.1; 524/131; 524/148

(58) Field of Classification Search
USPC ...................... 526/144; 424/9.1; 524/131, 148
See application file for complete search history.

(56) References Cited

U.S. PATENT DOCUMENTS

| | | |
|---|---|---|
| 2,713,593 A | 7/1955 | Brice et al. |
| 3,250,808 A | 5/1966 | Moore, Jr. et al. |
| 3,271,341 A | 9/1966 | Garrison |
| 3,274,244 A | 9/1966 | Mackenzie |
| 3,306,855 A | 2/1967 | Borecki |
| 3,391,099 A | 7/1968 | Punderson |
| 3,451,908 A | 6/1969 | Sianesi et al. |
| 3,492,374 A | 1/1970 | Le Bleu |
| 3,536,710 A | 10/1970 | Bartlett |
| 3,553,179 A | 1/1971 | Bartlett |
| 3,555,089 A | 1/1971 | Bartlett |
| 3,555,100 A | 1/1971 | Garth et al. |
| 3,589,906 A | 6/1971 | McDowell |
| 3,621,059 A | 11/1971 | Bartlett |
| 3,644,492 A | 2/1972 | Bartlett |
| 3,646,085 A | 2/1972 | Bartlett |
| 3,721,696 A | 3/1973 | Sianesi et al. |
| 3,798,265 A | 3/1974 | Bartlett |
| 3,810,874 A | 5/1974 | Mitsch et al. |
| 3,839,425 A | 10/1974 | Bartlett |
| 3,927,072 A | 12/1975 | Fox |
| 4,025,709 A | 5/1977 | Blaise et al. |
| 4,089,804 A | 5/1978 | Falk |
| 4,292,402 A | 9/1981 | Pollet et al. |
| 4,380,618 A | 4/1983 | Khan et al. |
| 4,381,384 A | 4/1983 | Khan |
| 4,544,458 A | 10/1985 | Grot et al. |
| 4,588,796 A | 5/1986 | Wheland |
| 4,621,116 A | 11/1986 | Morgan |
| 4,766,190 A | 8/1988 | Morita et al. |
| 4,789,717 A | 12/1988 | Giannetti et al. |
| 4,832,879 A | 5/1989 | Hamprecht |
| 4,861,845 A | 8/1989 | Slocum et al. |
| 4,864,006 A | 9/1989 | Giannetti et al. |
| 4,987,254 A | 1/1991 | Schwertfeger et al. |
| 5,130,477 A | 7/1992 | Koike et al. |
| 5,132,446 A | 7/1992 | Tohzuka et al. |
| 5,153,322 A | 10/1992 | Flynn |
| 5,256,318 A | 10/1993 | Masutani et al. |
| 5,285,002 A | 2/1994 | Grootaert |
| 5,350,497 A | 9/1994 | Hung et al. |
| 5,395,657 A | 3/1995 | Strepparola et al. |

(Continued)

FOREIGN PATENT DOCUMENTS

| | | | |
|---|---|---|---|
| CA | 761007 | * | 6/1967 |
| DE | 3 828 063 | | 2/1990 |
| EP | 0 519 406 | | 12/1992 |
| EP | 0 525 660 | | 2/1993 |
| EP | 0 625 526 A1 | | 11/1994 |
| EP | 0 712 882 | | 5/1996 |
| GB | 1 194 431 | | 6/1970 |
| GB | 1 352 560 | | 5/1974 |
| JP | 2002-308914 | | 10/2002 |
| JP | 2002-308914 A | * | 10/2002 |

(Continued)

OTHER PUBLICATIONS

Tonelli, et al., "Linear Perfluoropolyether Difunctional Oligomers: Chemistry, Properties and Applications", J. Fluorine Chem., 1999, vol. 95, pp. 51-70.*

England, "Catalytic Conversion of Fluoroalkyl Alkyl Ethers to Carbonyl Compounds", J. Org. Chem., 1984, vol. 49, pp. 4007-4008.

(Continued)

*Primary Examiner* — Peter D. Mulcahy
*Assistant Examiner* — Henry Hu

(57) ABSTRACT

Compounds represented by formula $(Rf\text{-}Q\text{-}X)_s\text{-}Z$. Each Rf is independently a partially fluorinated or fully fluorinated group selected from $Rf^a\text{-}(O)_r\text{-}CHF\text{-}(CF_2)_n\text{-}$; $[Rf^b\text{-}(O)_rC(L)H\text{-}CF_2\text{-}O]_m\text{-}W\text{-}$; $CF_3CFH\text{-}O\text{-}(CF_2)_p\text{-}$; $CF_3\text{-}(O\text{-}CF_2)_z\text{-}$; and $CF_3\text{-}O\text{-}(CF_2)_3\text{-}O\text{-}CF_2\text{-}$. Methods of reducing surface tension of a liquid, making foams, and treating a surface using the compounds are also disclosed.

16 Claims, No Drawings

(56) References Cited

U.S. PATENT DOCUMENTS

| | | | |
|---|---|---|---|
| 5,399,718 A | 3/1995 | Costello et al. | |
| 5,414,102 A | 5/1995 | Pohmer et al. | |
| 5,424,474 A | 6/1995 | Pohmer et al. | |
| 5,453,539 A | 9/1995 | Kondo et al. | |
| 5,488,142 A | 1/1996 | Fall et al. | |
| 5,498,680 A | 3/1996 | Abusleme et al. | |
| 5,502,251 A | 3/1996 | Pohmer et al. | |
| 5,503,967 A | 4/1996 | Furlan | |
| 5,532,310 A | 7/1996 | Grenfell et al. | |
| 5,536,425 A | 7/1996 | Kondo | |
| 5,550,277 A | 8/1996 | Paciorek et al. | |
| 5,656,201 A | 8/1997 | Visca et al. | |
| 5,663,255 A | 9/1997 | Anolick et al. | |
| 5,688,884 A | 11/1997 | Baker et al. | |
| 5,710,345 A | 1/1998 | Navarrini | |
| 5,763,552 A | 6/1998 | Feiring et al. | |
| 5,789,508 A | 8/1998 | Baker et al. | |
| 5,959,026 A | 9/1999 | Abusleme et al. | |
| 6,013,712 A | 1/2000 | Chittofrati et al. | |
| 6,013,795 A | 1/2000 | Manzara et al. | |
| 6,025,307 A | 2/2000 | Chittofrati et al. | |
| 6,103,843 A | 8/2000 | Abusleme et al. | |
| 6,127,498 A | 10/2000 | Tonelli et al. | |
| 6,184,187 B1 | 2/2001 | Howell et al. | |
| 6,255,536 B1 | 7/2001 | Worm et al. | |
| 6,297,334 B1 | 10/2001 | Marchese et al. | |
| 6,395,848 B1 | 5/2002 | Morgan et al. | |
| 6,410,626 B1 | 6/2002 | Wada et al. | |
| 6,429,258 B1 | 8/2002 | Morgan et al. | |
| 6,452,038 B1 | 9/2002 | Rao et al. | |
| 6,482,979 B1 | 11/2002 | Hintzer et al. | |
| 6,512,063 B2 | 1/2003 | Tang | |
| 6,576,703 B2 | 6/2003 | Kapeliouchko et al. | |
| 6,602,968 B1 | 8/2003 | Bekiarian et al. | |
| 6,613,860 B1 | 9/2003 | Dams et al. | |
| 6,624,268 B1 | 9/2003 | Maekawa et al. | |
| 6,632,508 B1 | 10/2003 | Pellerite et al. | |
| 6,642,307 B1 | 11/2003 | Sogabe et al. | |
| 6,646,088 B2 | 11/2003 | Fan et al. | |
| 6,656,258 B2 | 12/2003 | Elsbernd et al. | |
| 6,660,798 B1 | 12/2003 | Marchese et al. | |
| 6,677,414 B2 | 1/2004 | Hintzer et al. | |
| 6,689,854 B2 | 2/2004 | Fan et al. | |
| 6,693,152 B2 | 2/2004 | Kaspar et al. | |
| 6,703,520 B2 | 3/2004 | Hintzer et al. | |
| 6,716,534 B2 | 4/2004 | Moore et al. | |
| 6,730,760 B2 | 5/2004 | Grootaert et al. | |
| 6,737,489 B2 | 5/2004 | Linert et al. | |
| 6,750,304 B2 | 6/2004 | Kaspar et al. | |
| 6,774,164 B2 | 8/2004 | Lyons et al. | |
| 6,815,040 B2 | 11/2004 | Pellerite et al. | |
| 6,822,059 B2 | 11/2004 | Buckanin et al. | |
| 6,833,418 B2 | 12/2004 | Tan et al. | |
| 6,878,772 B2 | 4/2005 | Visca et al. | |
| 6,923,921 B2 | 8/2005 | Flynn et al. | |
| 7,041,728 B2 | 5/2006 | Zipplies et al. | |
| 7,045,571 B2 | 5/2006 | Tan et al. | |
| 7,064,170 B2 | 6/2006 | Kaspar et al. | |
| 7,074,862 B2 | 7/2006 | Kaspar et al. | |
| 7,094,829 B2 | 8/2006 | Audenaert et al. | |
| 7,097,910 B2 | 8/2006 | Moore et al. | |
| 7,122,608 B1 | 10/2006 | Brinati et al. | |
| 7,125,941 B2 | 10/2006 | Kaulbach et al. | |
| 7,126,016 B2 | 10/2006 | Fu et al. | |
| 7,141,537 B2 | 11/2006 | Audenaert et al. | |
| 7,214,736 B2 | 5/2007 | Audenaert et al. | |
| 7,279,522 B2 | 10/2007 | Dadalas et al. | |
| 7,297,744 B2 | 11/2007 | Kapeliouchko et al. | |
| 7,342,066 B2 | 3/2008 | Dadalas et al. | |
| 7,351,342 B2 | 4/2008 | Funaki et al. | |
| 7,425,279 B2 | 9/2008 | Cote et al. | |
| 7,566,762 B2 | 7/2009 | Otsuka et al. | |
| 7,659,333 B2 * | 2/2010 | Hintzer et al. | 524/156 |
| 7,671,112 B2 | 3/2010 | Hintzer et al. | |
| 7,678,426 B2 | 3/2010 | Flynn et al. | |
| 7,696,268 B2 | 4/2010 | Tsuda | |
| 7,745,653 B2 | 6/2010 | Iyer et al. | |
| 7,754,795 B2 | 7/2010 | Hintzer et al. | |
| 7,776,946 B2 | 8/2010 | Hintzer et al. | |
| 7,795,375 B2 | 9/2010 | Shirakawa et al. | |
| 7,803,894 B2 | 9/2010 | Dams et al. | |
| 7,838,608 B2 | 11/2010 | Hintzer et al. | |
| 8,002,886 B2 | 8/2011 | Clark | |
| 2002/0091212 A1 | 7/2002 | Abusleme et al. | |
| 2003/0181572 A1 * | 9/2003 | Tan et al. | 524/502 |
| 2004/0010156 A1 | 1/2004 | Kondo et al. | |
| 2004/0077237 A1 | 4/2004 | Audenaert et al. | |
| 2004/0116742 A1 | 6/2004 | Guerra | |
| 2004/0242755 A1 * | 12/2004 | Araki et al. | 524/462 |
| 2005/0090613 A1 | 4/2005 | Maruya et al. | |
| 2005/0154104 A1 | 7/2005 | Malvasi et al. | |
| 2005/0228127 A1 | 10/2005 | Tatemoto et al. | |
| 2006/0281946 A1 | 12/2006 | Morita et al. | |
| 2007/0004848 A1 | 1/2007 | Hintzer et al. | |
| 2007/0015864 A1 | 1/2007 | Hintzer et al. | |
| 2007/0015865 A1 | 1/2007 | Hintzer et al. | |
| 2007/0117915 A1 * | 5/2007 | Funaki et al. | 524/544 |
| 2007/0155891 A1 | 7/2007 | Tsuda et al. | |
| 2007/0276103 A1 * | 11/2007 | Guerra et al. | 526/144 |
| 2008/0015304 A1 | 1/2008 | Hinter et al. | |
| 2008/0015319 A1 | 1/2008 | Hintzer et al. | |
| 2009/0149616 A1 | 6/2009 | Audenaert et al. | |
| 2010/0168300 A1 | 7/2010 | Dams et al. | |
| 2010/0179262 A1 | 7/2010 | Dams et al. | |
| 2011/0124532 A1 | 5/2011 | Maurer et al. | |

FOREIGN PATENT DOCUMENTS

| | | | |
|---|---|---|---|
| JP | 2002-317003 | | 10/2002 |
| JP | 2003-027079 | | 1/2003 |
| JP | 2003-043625 | | 2/2003 |
| JP | 2003-119204 | * | 4/2003 |
| JP | 2003-212919 | | 7/2003 |
| JP | 2004-018394 | | 1/2004 |
| JP | 2004-358397 | | 12/2004 |
| JP | 2004-359870 | | 12/2004 |
| JP | 2007-106958 | | 4/2007 |
| WO | WO 98/50603 | | 11/1998 |
| WO | WO 02/20676 | | 3/2002 |
| WO | WO 2005/063827 | | 7/2005 |
| WO | WO 2005/065800 | | 7/2005 |
| WO | WO 2005/092520 | | 10/2005 |
| WO | WO 2005/121290 | | 12/2005 |
| WO | WO-2005/121290 A1 | * | 12/2005 |
| WO | WO 2005/123646 | | 12/2005 |

OTHER PUBLICATIONS

Chi et al., "A Facile Synthesis of Partly-fluorinated Ethers Using Perfluoroporpoxyethylene and Aliphatic Alcohols", Bull. Korean Chem. Soc., 1999, vol. 20, No. 2, pp. 220-222.

"Synthesis of Perfluoroalkyl Vinyl Ether Acids and Derivatives," Perfluoroalkyl Vinyl Ether Acids. Raymond Sullivan, vol. 34, No. 6, Jun. 1969, p. 1841-1844.

Karsa, "Industrial Applications of Surfactants", The Proceedings of a Symposium organized by the North West Region of the Industrial Division of the Royal Society of Chemistry, The Royal Society of Chemistry, Burlington House, London, 343 pages (1987).

Rosen, "Surfactants and Interfacial Phenomena", John Wiley & Sons, NY, 295 pages (1978).

International Search Report from PCT/US2009/050267; 5 pgs.

Tonelli, "Linear Perfluoropolyether Difunctional Oligomers: Chemistry, Properties and Applications", J. Fluorine Chem., 1999, vol. 95, pp. 51-70.

* cited by examiner

FLUORINATED ETHER COMPOUNDS AND METHODS OF USING THE SAME

CROSS REFERENCE TO RELATED APPLICATIONS

This application is a national stage filing under 35 U.S.C. 371 of PCT/US2009/050627, filed Jul. 15, 2009, which claims priority to U.S. Provisional Application Ser. No. 61/081,942, filed Jul. 18, 2008, the disclosure of which is incorporated herein by reference in its entirety.

BACKGROUND

Fluorochemicals have been used in a variety of applications for many years. For example, fluorinated surfactants have been added to a variety of formulations (e.g., coatings and foams). The addition of a fluorinated surfactant to a formulation (e.g., a coating formulation) may enhance the properties of the formulation by improving, for example, wetting behavior, leveling properties, and stability (e.g., with respect to phase separation or foam half-life). In other applications, fluorochemicals have been used to provide properties such as hydrophobicity and oleophobicity to various materials (e.g., ceramics, metals, fabrics, plastics, and porous stones).

Traditionally, many widely used fluorinated surfactants and repellents include long-chain perfluoroalkyl groups, (e.g., perfluorooctyl groups). Recently, however, there has been an industry trend away from using perfluorooctyl fluorinated surfactants, which has resulted in a desire for new types of surfactants which may be used in a variety of applications.

SUMMARY

The present disclosure provides compounds that have partially fluorinated polyether groups and/or fully fluorinated polyether groups with a low number (e.g., up to 4) continuous perfluorinated carbon atoms. The compounds may be useful, for example, as surfactants or surface treatments. In some embodiments, the compounds disclosed herein unexpectedly lower the surface tension of water to an extent comparable to or higher than fully fluorinated surfactants having a greater number of perfluorinated carbon atoms. In some embodiments, the compounds disclosed herein unexpectedly raise the contact angle versus water and/or hexadecane to an extent comparable to treatment compositions having a greater number of perfluorinated carbon atoms.

In one aspect, the present disclosure provides a compound represented by formula:

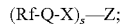

wherein
Rf is selected from the group consisting of:
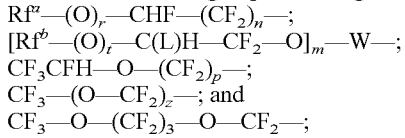

Q is selected from the group consisting of a bond, —C(O)O⁻ ⁺NH(R')₂—, —C(O)—N(R')—, and —C(O)—O—, wherein R' is selected from the group consisting of hydrogen and alkyl having from 1 to 4 carbon atoms;
X is selected from the group consisting of alkylene, arylalkylene, and poly(alkyleneoxy) wherein alkylene and arylalkylene are each optionally interrupted by at least one functional group independently selected from the group consisting of ether, amine, ester, amide, carbamate, and urea;
Z is selected from the group consisting of an ammonium group, an amine-oxide group, an amine, a carboxylate, a sulfonate, a sulfate, phosphate, a phosphonate, and an amphoteric group, with the proviso that when X is alkylene having at least 10 carbon atoms, Z may also be hydrogen, and with the further proviso that when X is poly(alkyleneoxy), Z may also be selected from the group consisting of hydroxyl and alkoxy;
Rf$^a$ and Rf$^b$ independently represent a partially or fully fluorinated alkyl group having from 1 to 10 carbon atoms and optionally interrupted with at least one oxygen atom;
L is selected from the group consisting of F and CF₃;
W is selected from the group consisting of alkylene and arylene;
r is 0 or 1, wherein when r is 0, then Rf$^a$ is interrupted with at least one oxygen atom;
s is 1 or 2, wherein when s is 2, then Z is selected from the group consisting of an ammonium group, a phosphate, a sulfate, and a phosphonate;
t is 0 or 1;
m is 1, 2, or 3;
n is 0 or 1;
each p is independently a number from 1 to 6; and
z is a number from 2 to 7.

In another aspect, the present disclosure provides a composition comprising a compound disclosed herein and at least one of solvent or water. In some embodiments, the composition further comprises a non-fluorinated polymer.

In another aspect, the present disclosure provides a method comprising treating a surface with a composition comprising a compound disclosed herein and at least one of solvent or water. In some embodiments, the surface comprises at least one of a polymer, ceramic (i.e., glasses, crystalline ceramics, glass ceramics, and combinations thereof), stone such as natural stone (e.g., sandstone, limestone, marble, and granite) or manmade or engineered stone, concrete, laminate, metal, or wood. In some of these embodiments, Z is a phosphate or phosphonate group.

In another aspect, the present disclosure provides an article having a surface, wherein at least a portion of the surface is in contact with a compound disclosed herein. In some embodiments, the surface comprises at least one of a polymer, ceramic (i.e., glasses, crystalline ceramics, glass ceramics, and combinations thereof), stone such as natural stone (e.g., sandstone, limestone, marble, and granite) or manmade or engineered stone, concrete, laminate, metal, or wood. In some of these embodiments, Z is a phosphate or phosphonate group.

In another aspect, the present disclosure provides a method of reducing the surface tension of a liquid, the method comprising combining at least the liquid with an amount of a compound disclosed herein sufficient to reduce the surface tension of the liquid.

In another aspect, the present disclosure provides methods of making a foam, the method comprising combining at least a liquid, a gas, and a compound according to the present disclosure to make the foam. In some of these embodiments, the liquid is water.

In some of these embodiments, the liquid is a hydrocarbon liquid.

In this application:
The terms "a", "an", and "the" are used interchangeably with the term "at least one".

The phrase "at least one of" followed by a list refers to any one of the items in the list and any combination of two or more items in the list.

"Alkyl group" and the prefix "alk-" are inclusive of both straight chain and branched chain groups and of cyclic groups. In some embodiments, alkyl groups have up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms.

"Alkylene" is the divalent form of the "alkyl" groups defined above.

"Arylalkylene" refers to an "alkylene" moiety to which an aryl group is attached.

The term "aryl" as used herein includes carbocyclic aromatic rings or ring systems, for example, having 1, 2, or 3 rings and optionally containing at least one heteroatom (e.g., O, S, or N) in the ring. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

"Arylene" is the divalent form of the "aryl" groups defined above.

In this application, all numerical ranges are inclusive of their endpoints and non-integral values between the endpoints unless otherwise stated.

DETAILED DESCRIPTION

For compounds represented by formula $(Rf-Q-X)_s$—Z, Rf is selected from the group consisting of:

$$Rf^a-(O)_r-CHF-(CF_2)_n- \quad \text{I;}$$

$$[Rf^b-(O)_t-C(L)H-CF_2-O]_m-W- \quad \text{II;}$$

$$CF_3CFH-O-(CF_2)_p- \quad \text{III;}$$

$$CF_3-(O-CF_2)_z- \quad \text{IV; and}$$

$$CF_3-O-(CF_2)_3-O-CF_2- \quad \text{V.}$$

In some embodiments of Formula $(Rf-Q-X)_s$—Z, Rf is selected from the group consisting of $Rf^a-(O)_r-CHF-(CF_2)_n-$, $[Rf^b-(O)_t-C(L)H-CF_2-O]_m-W-$, and $CF_3CFH-O-(CF_2)_p-$. In some embodiments of Formula $(Rf-Q-X)_s$—Z, Rf is selected from the group consisting of $CF_3-(O-CF_2)_z-$ and $CF_3-O-(CF_2)_3-O-CF_2-$.

In some embodiments of Formula $(Rf-Q-X)_s$—Z, Rf has a molecular weight of up to 600 grams per mole (in some embodiments, up to 500, 400, or even up to 300 grams per mole).

In Formulas I and II, $Rf^a$ and $Rf^b$ independently represent a partially or fully florinated alkyl group having from 1 to 10 carbon atoms and optionally interrupted with at least one oxygen atom. $Rf^a$ and $Rf^b$ include linear and branched alkyl groups. In some embodiments, $Rf^a$ and/or $Rf^b$ is linear. In some embodiments, $Rf^a$ and $Rf^b$ independently represent a fully fluorinated (i.e., perfluorinated) alkyl group having up to 6 (in some embodiments, 5, 4, 3, 2, or 1) carbon atoms. In some embodiments, $Rf^a$ and $Rf^b$ independently represent a fully fluorinated alkyl group interrupted with at least one oxygen atom, of which the alkyl groups between oxygen atoms have up to 6 (in some embodiments, 5, 4, 3, 2, or 1) carbon atoms, and wherein the terminal alkyl group has up to 6 (in some embodiments, 5, 4, 3, 2, or 1) carbon atoms. In some embodiments, $Rf^a$ and $Rf^b$ independently represent a partially fluorinated alkyl group having up to 6 (in some embodiments, 5, 4, 3, 2, or 1) carbon atoms and up to 2 hydrogen atoms. In some embodiments, $Rf^a$ and $Rf^b$ independently represent a partially fluorinated alkyl group having up to 2 hydrogen atoms interrupted with at least one oxygen atom, of which the alkyl groups between oxygen atoms have up to 6 (in some embodiments, 5, 4, 3, 2, or 1) carbon atoms, and wherein the terminal alkyl group has up to 6 (in some embodiments, 5, 4, 3, 2, or 1) carbon atoms.

In some embodiments of Formulas I and II, $Rf^a$ and $Rf^b$ are independently represented by formula $$R_f^1-[OR_f^2]_x-[OR_f^3]_y-.$$

$R_f^1$ is a perfluorinated alkyl group having from 1 to 6 (in some embodiments, 1 to 4) carbon atoms. $R_f^2$ and $R_f^3$ are each independently perfluorinated alkylene having from 1 to 4 carbon atoms. x and y are each independently numbers from 0 to 4, and the sum of x and y is at least 1. In some of these embodiments, t is 1, and r is 1.

In some embodiments of Formulas I and II, $Rf^a$ and $Rf^b$ are independently represented by formula $$R_f^4-[OR_f^5]_a-[OR_f^6]_b-O-CF_2-.$$

$R_f^4$ is a perfluorinated alkyl group having from 1 to 6 (in some embodiments, 1 to 4) carbon atoms. $R_f^5$ and $R_f^6$ are each independently perfluorinated alkylene having from 1 to 4 carbon atoms. a and b are each independently numbers from 0 to 4. In some of these embodiments, t is 0, and r is 0.

In some embodiments of Formulas I and II, $Rf^a$ and $Rf^b$ are independently represented by formula $R_f^7-(OCF_2)_p-$, wherein p is from 1 to 6 (in some embodiments, 1 to 4), and $R_f^7$ is selected from the group consisting of a partially fluorinated alkyl group having 1, 2, 3, 4, 5, or 6 carbon atoms and 1 or 2 hydrogen atoms and a fully fluorinated alkyl group having 1, 2, 3 or 4 carbon atoms.

In some embodiments of Formulas I and II, $Rf^a$ and $Rf^b$ are independently represented by formula $R_f^8-O-(CF_2)_p-$, wherein p is from 1 to 6 (in some embodiments, 1 to 4) and $R_f^8$ is selected from the group consisting of a partially fluorinated alkyl group having 1, 2, 3, 4, 5, or 6 carbon atoms and 1 or 2 hydrogen atoms and a fully fluorinated alkyl group having 1, 2, 3 or 4 carbon atoms.

In Formula II, L is selected from the group consisting of F and $CF_3$. In some embodiments of Formula II, L is F. In other embodiments, L is $CF_3$.

In Formula II, W is selected from the group consisting of alkylene and arylene. Alkylene includes linear, branched, and cyclic alkylene groups having from 1 to 10 (in some embodiments, 1 to 4) carbon atoms. In some embodiments, W is methylene. In some embodiments, W is ethylene. Arylene includes groups having 1 or 2 aromatic rings, optionally having at least one heteroatom (e.g., N, O, and S) in the ring, and optionally substituted with at least one alkyl group or halogen atom. In some embodiments, W is phenylene.

In Formulas II, t is 0 or 1. In some embodiments, t is 1. In some embodiments, t is 0. In embodiments wherein t is 0, $Rf^b$ is typically interrupted by at least one oxygen atom.

In Formula II, m is 1, 2, or 3. In some embodiments, m is 1.

In Formula I, n is 0 or 1. In some embodiments, n is 0. In some embodiments, n is 1.

In Formulas III, p is a number from 1 to 6 (i.e., 1, 2, 3, 4, 5, or 6). In some embodiments, p is 1, 2, 5, or 6. In some embodiments, p is 3. In some embodiments, p is 1 or 2. In some embodiments, p is 5 or 6.

In Formula IV, z is a number from 2 to 7 (i.e., 2, 3, 4, 5, 6, or 7). In some embodiments, z is a number from 2 to 6, 2 to 5, 2 to 4, or 3 to 4.

In some embodiments, compounds according to the present disclosure have an Rf group represented by Formula III (i.e., $CF_3CFH-O-(CF_2)_p-$). In some of these embodiments Rf is selected from the group consisting of $CF_3CFH-O-(CF_2)_3-$ and $CF_3CFH-O-(CF_2)_5-$.

In some embodiments, compounds according to the present disclosure have an Rf group represented by Formula I. In some of these embodiments, Rf is selected from the group consisting of:

$CF_3$—O—CHF—;

$CF_3$—O—$CF_2CF_2$—$CF_2$—O—CHF—;

$CF_3CF_2CF_2$—O—$CF_2CF_2$—$CF_2$—O—CHF—;

$CF_3$—O—$CF_2$—$CF_2$—O—CHF—;

$CF_3$—O—$CF_2$—O—$CF_2$—$CF_2$—O—CHF—;

$CF_3$—(O—$CF_2$)$_2$—O—$CF_2$—$CF_2$—O—CHF—; and $CF_3$—(O—$CF_2$)$_3$—O—$CF_2$—$CF_2$—O—CHF—.

In other of these embodiments, Rf is selected from the group consisting of:

$CF_3$—O—CHF—$CF_2$—;

$CF_3$—O—$CF_2$—$CF_2$—O—CHF—$CF_2$—;

$CF_3$—$CF_2$—O—CHF—$CF_2$—;

$CF_3$—O—$CF_2$—$CF_2$—$CF_2$—O—CHF—$CF_2$—;

$CF_3$—O—$CF_2$—O—$CF_2$—$CF_2$—O—CHF—$CF_2$—;

$CF_3$—(O—$CF_2$)$_2$—O—$CF_2$—$CF_2$—O—CHF—$CF_2$—; and $CF_3$—(O—$CF_2$)$_3$—O—$CF_2$—$CF_2$—O—CHF—$CF_2$—.

In other of these embodiments, Rf is selected from the group consisting of:

$CF_3$—O—$CF_2$—CHF—;

$C_3F_7$—O—$CF_2$—CHF—;

$CF_3$—O—$CF_2$—$CF_2$—$CF_2$—O—$CF_2$—CHF—;

$CF_3$—O—$CF_2$—O—$CF_2$—$CF_2$—O—$CF_2$—CHF—;

$CF_3$—(O—$CF_2$)$_2$—O—$CF_2$—$CF_2$—O—$CF_2$—CHF—; and $CF_3$—(O—$CF_2$)$_3$—O—$CF_2$—$CF_2$—O—$CF_2$—CHF—.

In other of these embodiments, Rf is selected from the group consisting of:

$CF_3$—O—$CF_2$—CHF—$CF_2$—;

$C_2F_5$—O—$CF_2$—CHF—$CF_2$—;

$C_3F_7$—O—$CF_2$—CHF—$CF_2$—;

$CF_3$—O—$CF_2$—$CF_2$—$CF_2$—O—$CF_2$—CHF—$CF_2$—;

$CF_3$—O—$CF_2$—O—$CF_2$—$CF_2$—O—$CF_2$—CHF—$CF_2$—;

$CF_3$—(O—$CF_2$)$_2$—O—$CF_2$—$CF_2$—O—$CF_2$—CHF—$CF_2$—; and $CF_3$—(O—$CF_2$)$_3$—O—$CF_2$—$CF_2$—O—$CF_2$—CHF—$CF_2$—.

In other of these embodiments, Rf is selected from the group consisting of:

$CF_3$—O—$CF_2CF_2$—$CF_2$—O—CHF—;

$CF_3$—O—$CF_2$—$CF_2$—$CF_2$—O—CHF—$CF_2$—;

$CF_3$—O—$CF_2$—$CF_2$—$CF_2$—O—$CF_2$—CHF—; and $CF_3$—O—$CF_2$—$CF_2$—$CF_2$—O—$CF_2$—CHF—$CF_2$—.

In some embodiments, compounds according to the present disclosure have an Rf group represented by Formula II. In some of these embodiments, L is F, m is 1, and W is alkylene. In some of these embodiments, Rf is selected from the group consisting of:

$CF_3$—O—CHF—$CF_2$—O—$CH_2$—;

$CF_3$—O—$CF_2$—$CF_2$—$CF_2$—O—CHF—$CF_2$—O—$CH_2$;

$C_3F_7$—O—CHF—$CF_2$—O—$CH_2$—;

$C_3F_7$—O—CHF—$CF_2$—O—$CH_2$—$CH_2$—;

$C_3F_7$—O—$CF_2$—$CF_2$—O—CHF—$CF_2$—$OCH_2$—; and $C_3F_7$—O—$CF_2$—$CF_2$—$CF_2$—O—CHF—$CF_2$—$OCH_2$—.

In other of these embodiments, Rf is represented by formula $C_3F_7$—O—$CF_2$—CHF—$CF_2$—$OCH_2$—. In other of these embodiments, Rf is selected from the group consisting of:

$CF_3$—CHF—$CF_2$—O—$CH_2$—; and $C_3F_7$—$CF_2$—CHF—$CF_2$—$OCH_2$—.

In some embodiments, compounds according to the present disclosure have an Rf group represented by Formula IV (i.e., $CF_3$—(O—$CF_2$)$_z$—). In some of these embodiments, z is a number from 2 to 6, 2 to 5, 2 to 4, 3 to 5, or 3 to 4.

In some embodiments, compounds according to the present disclosure have an Rf represented by Formula V (i.e., $CF_3$—O—($CF_2$)$_3$—O—$CF_2$—).

In Formula (Rf-Q-X)$_s$—Z, Q is selected from the group consisting of a bond, —C(O)O⁻ ⁺NH(R')$_2$—, —C(O)—N (R')—, and —C(O)—O—, wherein R' is hydrogen or alkyl having 1 to 4 carbon atoms (e.g., methyl, ethyl, n-propyl, isopropyl, n-butyl, isobutyl, or sec-butyl). In some embodiments, Q is selected from the group consisting of —C(O)—N(R')— and —C(O)—O—. In some embodiments, Q is selected from the group consisting of a bond and —C(O)—N(R')—. In some embodiments, Q is —C(O)—N(R')—. In some embodiments, Q is —C(O)O⁻ ⁺NH(R')$_2$—. In some embodiments, R' is hydrogen or methyl. In some embodiments, R' is hydrogen. It should be understood that when Q is a bond, a compound represented by Formula (Rf-Q-X)$_s$—Z can also be represented by Formula (Rf—X)$_s$—Z.

In Formula (Rf-Q-X)$_s$—Z, X is selected from the group consisting of alkylene and arylalkylene, wherein alkylene and arylalkylene are each optionally interrupted by at least one functional group independently selected from the group consisting of ether (i.e., —O—), amine (i.e., —N(R)—), ester, (i.e., —O—C(O)— or —C(O)—O—), amide (i.e., —N(R')—C(O)— or —C(O)—N(R')—), carbamate (i.e., —N(R')—C(O)—O— or —O—C(O)—N(R')—), and urea (i.e., —N(R')—C(O)—N(R')—), wherein in any of these functional groups, R' is as defined in any of the above embodiments. In some embodiments, X is alkylene having up to 5 carbon atoms. In some embodiments, X is alkylene having at least 10 (e.g., at least 12, 15, 18, 20, 22, 25, 28, or 30) carbon atoms. In some embodiments, X is alkylene that is optionally interrupted by at least one ether group. In some of these embodiments, X is a poly(alkyleneoxy) group. In some of these embodiments, X is -[EO]$_f$—[R$^2$O]$_g$-[EO]$_f$— or —[R$^2$O]$_g$-[EO]$_f$[R$^2$O]$_g$—, wherein EO represents —CH$_2$CH$_2$O—; each R$^2$O independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O— (in some embodiments, —CH(CH$_3$)CH$_2$O—, or —CH$_2$CH(CH$_3$)O—); each f is independently from 1 to 150 (in some embodiments, from 7 to about 150, 14 to about 125, 5 to 15, or 9 to 13); and each g is independently from 0 to 55 (in some embodiments, from about 21 to about 54, 15 to 25, 9 to about 25, or 19 to 23).

In Formula (Rf-Q-X)$_s$—Z, Z is selected from the group consisting of an ammonium group, an amine-oxide group, an amine, a carboxylate (i.e., —CO$_2$Y), a sulfonate (i.e., —SO$_3$Y), a sulfate (i.e., —O—SO$_3$Y or (—O)$_2$—SO$_2$Y), phosphate (i.e., —O—P(O)(OY)$_2$ or (—O)$_2$—P(O)OY), a phosphonate (i.e., —P(O)(OY)$_2$), and an amphoteric group, with the proviso that when X is alkylene having at least 10 carbon atoms, Z may also be hydrogen, and with the further proviso that when X is poly(alkyleneoxy), Z may also be a hydroxyl (i.e., —OH) or alkoxy (i.e., —O—alkyl). Ammonium groups include those represented by formula —[N(R)$_3$]$^+$M$^-$, wherein each R is independently hydrogen, alkyl, or aryl, wherein alkyl and aryl are optionally substituted by at least one halogen, alkoxy, nitro, or nitrile group and aryl may additionally be optionally substituted by alkyl, and wherein M$^-$ is a counter anion. Ammonium groups also include ring systems having one or two aromatic or saturated rings and a positively charged nitrogen atom (e.g., pyrrolium, pyrimidinium, pyrazolium, isoxazolium, oxazolium, thiazolium, isothiazolium, pyridinium, pyrazinium, pyridazinium, imidazolium, isoindolium, indolium, purinium, quinolinium, isoquinolinium, naphthyridinium, quinoxalinium, quinazolinium, phthalazinium, indazolium, pyrrolidinium, piperidinium, azepinium, or piperazinium). Amine-oxide groups include those represented by formula —N(O)(R$^1$)$_2$, wherein each R$^1$ is independently hydrogen, alkyl, or aryl, wherein alkyl and aryl are optionally substituted as described above for R, and ring systems having one or two aromatic or saturated rings and an N-oxide (e.g., an N-oxide of pyrrolium, pyrimidinium, pyrazolium, isoxazolium, oxazolium, thiazolium, isothiazolium, pyridinium, pyrazinium, pyridazinium, imidazolium, isoindolium, indolium, purinium, quinolinium, isoquinolinium, naphthyridinium, quinoxalinium, quinazolinium, phthalazinium, indazolium, pyrrolidinium, piperidinium, azepinium, or piperazinium). Amines include those represented by formula —NR$_2$, wherein each R is independently hydrogen, alkyl, or aryl, wherein alkyl and aryl are optionally substituted as described above, or two R groups may join to form a 5 to 7-membered ring optionally containing at least one O, N, or S and optionally substituted by alkyl having 1 to 6 carbon atoms. Amphoteric groups include those having both an ammonium group and either a carboxylate, a sulfonate, a sulfate, phosphate, or a phosphonate group.

In some embodiments, Z is selected from the group consisting of an ammonium group, an amine-oxide group, a carboxylate, a sulfonate, a sulfate, phosphate, a phosphonate, and an amphoteric group. In some embodiments, Z is selected from the group consisting of an ammonium group, an amine-oxide group, and an amphoteric group. In some embodiments, Z is selected from the group consisting of a carboxylate, a sulfonate, a sulfate, phosphate, and a phosphonate.

In some embodiments of compounds represented by formula (Rf-Q-X)$_s$—Z, Z is selected from the group consisting of —[N(R)$_3$]$^+$M$^-$, —N(O)(R$^1$)$_2$, —N$^+$(R)$_2$—X$^1$—SO$_3$A, and —N$^+$(R)$_2$—X$^1$—CO$_2$A. In some of these embodiments, Z is —[N(R)$_3$]$^+$M$^-$. In other embodiments, Z is —N(O)(R$^1$)$_2$, —N$^+$(R)$_2$—X$^1$—SO$_3$A, or —N$^+$(R)$_2$—X$^1$—CO$_2$A.

In any of the above embodiments of Z, each R is independently selected from the group consisting of hydrogen and alkyl having from 1 to 6 carbon atoms (e.g., methyl, ethyl, n-propyl, isopropyl, n-butyl, isobutyl, sec-butyl, n-pentyl, isopentyl, neopentyl, or n-hexyl). In some embodiments, each R is independently hydrogen or methyl.

In any of the above embodiments of Z, each R$^1$ is independently selected from the group consisting of hydrogen and alkyl having from 1 to 6 carbon atoms (e.g., methyl, ethyl, n-propyl, isopropyl, n-butyl, isobutyl, sec-butyl, n-pentyl, isopentyl, neopentyl, or n-hexyl), wherein alkyl is optionally substituted by at least one halogen, alkoxy, nitro, or nitrile group, or two R$^1$ groups may join to form a 5 to 7-membered ring optionally containing at least one O, N, or S and optionally substituted by alkyl having 1 to 6 carbon atoms. In some embodiments, each R$^1$ is independently hydrogen or methyl.

In any of the above embodiments of Z, each X$^1$ is selected from the group consisting of alkylene and arylalkylene, wherein alkylene and arylalkylene are each optionally interrupted by at least one ether linkage. In some embodiments, X$^1$ is alkylene having up to 5 carbon atoms.

In any of the above embodiments of Z, M$^-$ is a counter anion. Typical counter anions include halides (i.e., fluoride, chloride, bromide, and iodide), organic acid salts (e.g., formate, acetate, propionate, lactate, laurate, palmitate, stearate, or citrate), organic sulfonic or sulfuric acid salts (e.g., alkyl sulfates or alkanesulfonates), nitrate, and tetrafluoroborate. The organic acid salts and sulfonic acid salts may be partially fluorinated or perfluorinated. In some embodiments, the acid salt is RfC(O)O$^-$, wherein Rf is as defined in any of the above embodiments. In some embodiments, M$^-$ is chloride, bromide, or iodide (i.e., Cl—, Br—, or I—). In some embodiments, M$^-$ is selected from the group consisting of chloride, acetate, iodide, bromide, methylsulfate, ethylsulfate, and formate.

In any of the above embodiments of Z, A is selected from the group consisting of hydrogen and a free anion.

In some embodiments of compounds represented by formula (Rf-Q-X)$_s$—Z, Z is selected from the group consisting of —P(O)(OY)$_2$, —O—P(O)(OY)$_2$, —SO$_3$Y, —O—SO$_3$Y, and —CO$_2$Y. In some embodiments, s is 2, and Z is (—O)$_2$—P(O)(OY). In some of these embodiments, Y is hydrogen. In other of these embodiments, Y is a counter cation. Exemplary Y counter cations include alkali metal (e.g., sodium, potassium, and lithium), alkaline earth metal (e.g., calcium and magnesium), ammonium, alkyl ammonium (e.g., tetraalkylammonium), and five to seven membered heterocyclic groups having a positively charged nitrogen atom (e.g, a pyrrolium ion, pyrazolium ion, pyrrolidinium ion, imidazolium ion, triazolium ion, isoxazolium ion, oxazolium ion, thiazolium ion, isothiazolium ion, oxadiazolium ion, oxatriazolium ion, dioxazolium ion, oxathiazolium ion, pyridinium ion, pyridazinium ion, pyrimidinium ion, pyrazinium ion, piperazinium ion, triazinium ion, oxazinium ion, piperidinium ion, oxathiazinium ion, oxadiazinium ion, and morpholinium ion). Interconversions of Y groups can be carried out, for example, using conventional acid-base chemistry.

In some embodiments of compounds according to the present disclosure, Z is —[N(R)$_3$]$^+$M$^-$, wherein each R and is independently hydrogen or methyl, and wherein M- is selected from the group consisting of chloride, acetate, iodide, bromide, methylsulfate, ethylsulfate, and formate.

In some embodiments of compounds according to the present disclosure, Q is —C(O)—N(R')—, and wherein X is alkylene having up to 5 (e.g., 1, 2, 3, 4, 5) carbon atoms.

In some embodiments of compounds according to the present disclosure, Q is —C(O)O$^-$ $^+$NH(R')$_2$—, and X is selected from the group consisting of alkylene having up to 5 carbon atoms, -[EO]$_f$—[R$^2$O]$_g$—[EO]$_f$—, and —[R$^2$O]$_g$—[EO]$_f$—[R$^2$O]$_g$—, wherein EO represents —CH$_2$CH$_2$O—; each R$^2$O independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O— (in some embodiments, —CH(CH$_3$)CH$_2$O—, or —CH$_2$CH(CH$_3$)O—); each f is independently a number from 1 to 150 (in some embodiments, from 7 to about 150, 14 to about 125, 5 to 15, or 9 to 13); and each g is independently a number from 0 to 55 (in some embodiments, from about 21 to about 54, 15 to 25, 9 to about 25, or 19 to 23). In some of these embodiments, the compound is represented by a formula selected from the group consisting of [Rf—C(O)O$^-$ $^+$NH(R')$_2$—X]$_2$—NH(R)$^+$ RfC(O)O$^-$ and Rf—C(O)O$^-$ $^+$NH(R')$_2$—X—NH(R)$_2$$^+$RfC(O)O$^-$, wherein each R is independently selected from the group consisting of hydrogen and alkyl having from 1 to 6 (e.g., from 1 to 4, 1 to 3, or 1 to 2) carbon atoms.

In some embodiments of compounds according to the present disclosure, Z is —N(O)(R$^1$)$_2$, —N$^+$(R)$_2$—X$^1$—SO$_3$A, or —N$^+$(R)$_2$—X$^1$—CO$_2$A, wherein each R and R$^1$ are independently hydrogen or methyl, and wherein X$^1$ is alkylene having up to 5 carbon atoms.

In some embodiments of compounds represented by Formula (Rf-Q-X)$_s$—Z, X—Z is selected from the group consisting of:

-[EO]$_f$—[R$^2$O]$_g$-[EO]$_f$—R$^3$; and

—[R$^2$O]$_g$-[EO]$_f$—[R$^2$O]$_g$—R$^3$, wherein
EO represents —CH$_2$CH$_2$O—;
each R$^2$O independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O— (in some embodiments, —CH(CH$_3$)CH$_2$O—, or —CH$_2$CH(CH$_3$)O—);
R$^3$ is hydrogen or alkyl having up to 4 carbon atoms (e.g., methyl, ethyl, n-propyl, isopropyl, n-butyl, sec-butyl, or isobutyl);
each f is independently from 1 to 150 (in some embodiments, from 7 to about 150, 14 to about 125, 5 to 15, or 9 to 13); and
each g is independently from 0 to 55 (in some embodiments, from about 21 to about 54, 15 to 25, 9 to about 25, or 19 to 23).

In some embodiments, each g is 0.

Compounds represented by Formula (Rf-Q-X)$_s$—Z can be prepared, for example, starting with a partially or fully fluorinated carboxylic acid, a salt thereof, a carboxylic acid ester, or a carboxylic acid halide. Partially and fully fluorinated carboxylic acids and salts thereof, carboxylic acid esters, and carboxylic acid halides can be prepared by known methods. For example, starting materials represented by formula Rf$^a$—(O)$_r$—CHF—(CF$_2$)$_n$—C(O)G or [Rf$^b$—(O)$_t$—C(L)H—CF$_2$—O]$_m$—W—C(O)G, wherein G represents —OH, —O—alkyl (e.g., having from 1 to 4 carbon atoms), or —F and Rf$^a$, Rf$^b$, n, m, L, t, r, and W are as defined in any of the embodiments above, can be prepared from fluorinated olefins of Formula VI or VII:

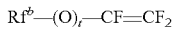 VI, or

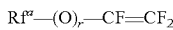 VII, wherein Rf$^a$, Rf$^b$, and t are as defined above. Numerous compounds of Formula VI or VII are known (e.g., perfluorinated vinyl ethers and perfluorinated allyl ethers), and many can be obtained from commercial sources (e.g., 3M Company, St. Paul, Minn., and E.I. du Pont de Nemours and Company, Wilmington, Del.). Others can be prepared by known methods; (see, e.g., U.S. Pat. Nos. 5,350,497 (Hung et al.) and 6,255,536 (Worm et al.)).

Compounds of formula Rf$^a$—(O)$_r$—CHF—(CF$_2$)$_n$—C(O)G, wherein n is 0, can be prepared, for example, by reacting a fluorinated olefin of Formula VII with a base (e.g., ammonia, alkali metal hydroxides, and alkaline earth metal hydroxides). Alternatively, for example, a fluorinated olefin of Formula VII can be reacted with an aliphatic alcohol (e.g., methanol, ethanol, n-butanol, and t-butanol) in an alkaline medium, and the resulting ether can be decomposed under acidic conditions to provide a fluorinated carboxylic acid of formula Rf$^a$—(O)$_r$—CHF—(CF$_2$)$_n$—C(O)G, wherein n is 0. Compounds of formula Rf$^a$—(O)$_r$—CHF—(CF$_2$)$_n$—C(O)G, wherein n is 1, can be prepared, for example, by a free radical reaction of the fluorinated olefin of Formula VII with methanol followed by an oxidation of the resulting reaction product using conventional methods. Conditions for these reactions are described, for example, in U.S. Pat. App. Pub. No. 2007/0015864 (Hintzer et al.), the disclosure of which, relating to the preparation of compounds of formula Rf$^a$—(O)$_r$—CHF—(CF$_2$)$_n$—C(O)G, is incorporated herein by reference. These methods may be useful, for example, for providing structurally pure compounds (e.g., free of other compounds containing other fluorinated segments). In some embodiments, compounds according to the present disclosure are at least 95% (e.g., 96, 97, 98, or 99%) pure.

Fluorinated vinyl ethers of Formulas VI or VII, wherein r and/or t is 1, can be oxidized (e.g., with oxygen) in the presence of a fluoride source (e.g., antimony pentafluoride) to carboxylic acid fluorides of formula Rf$^a$—O—CF$_2$C(O)F according to the methods described in U.S. Pat. No. 4,987,254 (Schwertfeger et al.), in column 1, line 45 to column 2, line 42, the disclosure of which is incorporated herein by reference. Examples of compounds that can be prepared according to this method include CF$_3$—(CF$_2$)$_2$—O—CF$_2$—C(O)—CH$_3$ and CF$_3$—O—(CF$_2$)$_3$—O—CF$_2$—C(O)—CH$_3$, which are described in U.S. Pat. App. Pub. No. 2007/0015864 (Hintzer et al.), the disclosure of which, relating to the preparation of these compounds, is incorporated herein by reference. These methods may be useful, for example, for providing structurally pure compounds (e.g., free of other compounds containing other fluorinated segments). In some embodiments, compounds according to the present disclosure are at least 95% (e.g., 96, 97, 98, or 99%) pure.

Compounds of formula [Rf$^b$—(O)$_t$—C(L)H—CF$_2$—O]$_m$—W—C(O)G can be prepared, for example, by reaction of a fluorinated olefin of Formula VI with a hydroxyl compound of Formula VIII according to the reaction:

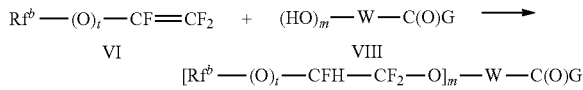

wherein Rf$^b$ and t are as defined above, m is 1, 2, or 3, W is alkylene or arylene, and G is as defined above. Typically, G represents —O-alkyl (e.g., having from 1 to 4 carbon atoms in the alkyl group). Compounds of Formula VIII can be obtained, for example, from commercial sources or can be prepared by known methods. The reaction can be carried out, for example, under conditions described in U.S. Pat. App. Pub. No. 2007/0015864 (Hintzer et al.), the disclosure of which, relating to the preparation of compounds of formula $[Rf^b\text{—}(O)_t\text{—}C(L)H\text{—}CF_2\text{—}O]_m\text{—}W\text{—}C(O)G$, is incorporated herein by reference.

Fluorinated carboxylic acids and their derivatives according to formula $CF_3CFH\text{—}O\text{—}(CF_2)_p\text{—}C(O)G$ can be prepared, for example, by decarbonylation of difunctional perfluorinated acid fluoride according to the reaction:

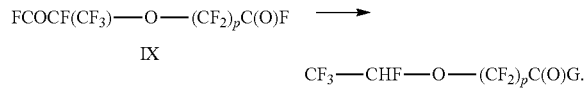

The reaction is typically carried out at an elevated temperature in the presence of water and base (e.g., a metal hydroxide or metal carbonate) according to known methods; see, e.g., U.S. Pat. No. 3,555,100 (Garth et al.), the disclosure of which, relating to the decarbonylation of difunctional acid fluorides, is incorporated herein by reference.

Compounds of Formula IX are available, for example, from the coupling of perfluorinated diacid fluorides of Formula X and hexafluoropropylene oxide according to the reaction:

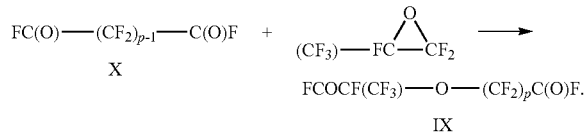

Compounds of Formula X are available, for example, by electrochemical fluorination or direct fluorination of a difunctional ester of formula $CH_3OCO(CH_2)_{p-1}COOCH_3$ or a lactone of formula:

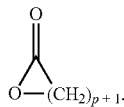

General procedures for carrying out electrochemical fluorination are described, for example, in U.S. Pat. No. 2,713,593 (Brice et al.) and International App. Pub. No. WO 98/50603, published Nov. 12, 1998. General procedures for carrying out direct fluorination are described, for example, in U.S. Pat. No. 5,488,142 (Fall et al.).

Some carboxylic acids and carboxylic acid fluorides useful for preparing compounds represented by formula $(Rf\text{-}Q\text{-}X)_s\text{—}Z$ are commercially available. For example, carboxylic acids of formula $CF_3[O\text{—}CF_2]_{1-3}C(O)OH$ are available from Anles Ltd., St. Petersburg, Russia.

Compounds represented by Formula $(Rf\text{-}Q\text{-}X)_s\text{—}Z$ can be prepared, for example, from a partially or fully fluorinated carboxylic acid or salt thereof, an acid fluoride thereof, or a carboxylic acid ester (e.g., $Rf\text{—}C(O)\text{—}OCH_3$) using a variety of conventional methods. For example, a methyl ester can be treated with an amine having formula $NH_2\text{—}X\text{—}Z$ according to the following reaction sequence.

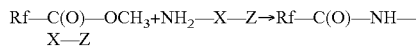

In this sequence, Rf, X, and Z are as defined in any of the above embodiments. Some amines having formula $NH_2\text{—}X\text{—}Z$ are commercially available, such as, amino acids (e.g., sarcosine, 7-aminoheptanoic acid, 12-aminododecanoic acid, and 3-aminopropylphosphonic acid), aliphatic amines (e.g., dodecylamine and hexadecylamine), and difunctional amines (e.g., 3-(dimethylamino)propylamine). The reaction may be carried out, for example, at an elevated temperature (e.g., up to 80° C., 70° C., 60° C., or 50° C.), and may be carried out neat or in a suitable solvent.

A compound represented by formula $Rf\text{—}C(O)\text{—}NH\text{—}X\text{—}Z$ can also be subjected to functional group transformations of the Z group using conventional techniques. For example, quaternary ammonium compounds according to the present disclosure, including compounds that contain an amphoteric group, can be prepared by using an amine having formula $NH_2\text{—}X\text{—}NR_2$ (e.g., 3-(dimethylamino)propylamine) in the first step to provide an amino-functionalized amide, which can then be quaternized by reaction with an acid (e.g., hydrochloric acid or acetic acid) or alkylating agents (e.g., diethylsulfate, propane sultone, iodomethane, bromobutane, or chloromethane). The reaction with an acid or an alkylating agent may be carried out at room temperature or at an elevated temperature (e.g., up to 60° C. or 50° C.). Or the amino-functionalized amide can be treated with hydrogen peroxide or a peracid (e.g., perbenzoic acid or peracetic acid) optionally at an elevated temperature (e.g., 60° C. to 70° C.) and in a suitable solvent (e.g., ethanol) to provide a compound of formula wherein Z is an amine oxide group.

Compounds represented by Formula $(Rf\text{-}Q\text{-}X)_s\text{—}Z$ can also be prepared, for example, by reaction of a carboxylic acid ester (e.g., $Rf\text{—}C(O)\text{—}OCH_3$) with an amino alcohol having formula $NH_2\text{—}X''\text{—}OH$ (e.g., ethanolamine) to prepare hydroxyl-substituted Rf-(CO)NHX"OH as shown in the following reaction sequence, wherein Rf is as defined in any of the above embodiments, s is 1 or 2, and X" is a precursor to X, wherein X is as defined in any of the above embodiments.

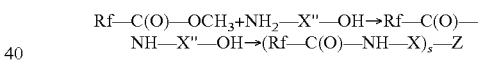

The conditions for the reaction with $NH_2\text{—}X\text{—}Z$, described above, can be used for the reaction with $NH_2\text{—}X''\text{—}OH$. The hydroxyl-substituted compound Rf-(CO)NHX"OH can then be treated with, for example, phosphonoacetic acid, phosphonopropionic acid, or phosphorous (V) oxychloride to provide phosphonates or phosphates according to the present disclosure. The reaction with phosphonoacetic acid or phosphonopropionic acid can be carried out, for example, in a suitable solvent (e.g., methyl isobutyl ketone or methyl ethyl ketone), optionally in the presence of a catalyst (e.g., methanesulfonic acid) and optionally at an elevated temperature (e.g., up to the reflux temperature of the solvent). The reaction of the hydroxyl-substituted compound represented by formula $Rf\text{—}C(O)\text{—}NH\text{—}X''\text{—}OH$ with phosphorous (V) oxychloride can be carried out, for example, in a suitable solvent (e.g., toluene), optionally at an elevated temperature (e.g., the reflux temperature of the solvent). One or two equivalents of the hydroxyl-substituted compound can be used provide compounds having formula $(Rf\text{—}C(O)\text{—}NH\text{—}X)_s\text{—}Z$, wherein Z is a phosphate, and s is 1 or 2. If one equivalent of the hydroxyl-substituted compound is used, an equivalent of water or alcohol may be added.

Compounds represented by Formula Rf-Q-X—Z can also be prepared, for example, by reducing an ester of formula $Rf\text{—}C(O)\text{—}OCH_3$ or a carboxylic acid of formula $Rf\text{—}C(O)\text{—}OH$ using conventional methods (e.g., hydride, such as sodium borohydride, reduction) to a hydroxyl-substituted compound of formula Rf—CH$_2$OH as shown in the following reaction sequence, wherein Rf, X, and Z are as defined in any of the above embodiments.

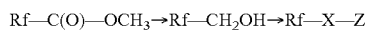

Rf—C(O)—OCH$_3$→Rf—CH$_2$OH→Rf—X—Z

The hydroxyl-substituted compound of formula Rf—CH$_2$OH can then be converted, for example, to a phosphate or phosphonate using any of the techniques described above.

Compounds according to the present disclosure can also be prepared, for example, by reaction of a carboxylic acid represented by formula Rf—C(O)—OH with an epoxide or mixture of epoxides according to the following reaction sequence, wherein Rf, f, g, and R$^3$ are as defined in any of the above embodiments and R$^4$ is hydrogen, methyl, ethyl, or a combination thereof.

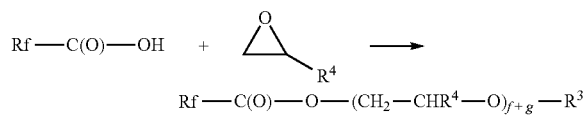

The reaction can be carried out, for example, in the presence of Lewis Acid catalysts such as complexes of boron trifluoride (e.g., boron trifluoride etherate, boron trifluoride tetrahydropyran, and boron trifluoride tetrahydrofuran), phosphorous pentafluoride, antimony pentafluoride, zinc chloride, and aluminum bromide. The reaction can also be carried out in the presence of (CF$_3$SO$_2$)$_2$CH$_2$. Ring-opening polymerizations can be carried out neat or in a suitable solvent such as a hydrocarbon solvent (e.g., toluene) or a halogenated solvent (e.g., dichloromethane, carbon tetrachloride, trichloroethylene, or dichloroethane). The reactions can be carried out at or near room temperature or below (e.g., in a range from about 0° C. to 40° C.). The reactions can also be carried out above room temperature (e.g, up to 40° C., 60° C., 70° C., 90° C., or up to the reflux temperature of the solvent).

Compounds according to the present disclosure can also be prepared, for example, by reaction of a carboxylic acid represented by formula Rf—C(O)—OH, wherein Rf is defined as in any of the above embodiments, with a diamine or triamine (e.g., 3-(dimethylamino)propylamine or diethylenetriamine). The equivalents of carboxylic acid and diamine or triamine can be adjusted to provide, mono-salts, di-salts, or tri-salts. For example, a carboxylic acid represented by formula Rf—C(O)—OH may be reacted with one equivalent of a diamine to provide a compound having formula Rf-Q-X—Z, wherein Q is —C(O)O$^-$ $^+$NH(R')$_2$—, and Z is an amine (e.g., a primary, secondary, or tertiary amine). Two equivalents of a carboxylic acid represented by formula Rf—C(O)—OH may also be reacted with a diamine to provide a compound, for example, having formula Rf-Q-X—Z, wherein Q is —C(O)O$^-$ $^+$NH(R)$_2$—, and Z is an ammonium group having formula —[NH(R)$_2$]$^+$RfC(O)O$^-$. In a further example, three equivalents of a carboxylic acid represented by formula Rf—C(O)—OH may be reacted with a triamine to provide a compound, for example, having formula (Rf-Q-X)$_2$—Z, wherein each Q is —C(O)O$^-$ $^+$NH(R')$_2$—, and Z is an ammonium group having formula (–)$_2$[NHR]$^+$RfC(O)O$^-$. The salts can be prepared, for example, by stirring a carboxylic acid and a diamine or triamine at room temperature or optionally at an elevated temperature and optionally in a suitable solvent (e.g., ethanol).

Compounds according to the present disclosure may be formulated into concentrates (e.g., in at least one of water or organic solvent), wherein the compound is present in an amount of at least 10, 20, 30, or even at least 40 percent by weight, based on the total weight of the concentrate. Techniques for preparing concentrates are known in the art.

In some embodiments, the present disclosure provides a composition comprising at least one of water or a water-miscible organic solvent and a compound according to the present disclosure. In some these embodiments, Z is selected from the group consisting of an ammonium group, an amine-oxide group, an amine, a hydroxyl, an alkoxy, a carboxylate, a sulfonate, a sulfate, phosphate, a phosphonate, and an amphoteric group.

In some embodiments, compositions according to and/or useful for practicing methods according to the present disclosure may comprise water and a non-fluorinated polymer. These aqueous compositions may be useful, for example, for coatings (e.g., floor finishes, varnishes, automotive coatings, marine coatings, sealers, hard coats for plastic lenses, coatings for metal cans or coils, and inks) When used in aqueous compositions (e.g., for coatings) compounds according to the present disclosure can be formulated into an aqueous solution or dispersion at a final concentration, for example, of about 0.001 to about 1 weight percent (wt. %), about 0.001 to about 0.5 wt. %, or about 0.01 to about 0.3 wt. %, based on the weight of the solution or dispersion. In some embodiments, compounds according to the present disclosure may enhance wetting and/or leveling of a coating (e.g., an aqueous coating) on a substrate surface and may provide better dispersability of a component (e.g., a thickening agent or pigment) within the coating composition.

In some embodiments, aqueous compositions comprising compounds according to the present disclosure (e.g., for coatings) include at least one non-fluorinated polymer, typically a film-forming polymer. Examples of suitable polymers include acrylic polymers, (e.g., poly(methyl methacrylate-co-ethyl acrylate) or poly(methyl acrylate-co-acrylic acid)); polyurethanes, (e.g., reaction products of aliphatic, cycloaliphatic or aromatic diisocyanates with polyester glycols or polyether glycols); polyolefins, (e.g., polystyrene); copolymers of styrene with acrylate(s) (e.g., poly(styrene-co-butyl acrylate); polyesters, (e.g, polyethylene terephthalate, polyethylene terephthalate isophthalate, or polycaprolactone); polyamides, (e.g., polyhexamethylene adipamide); vinyl polymers, (e.g., poly(vinyl acetate/methyl acrylate), poly(vinylidene chloride/vinyl acetate); polydienes, (e.g., poly(butadiene/styrene)); cellulosic derivatives including cellulose ethers and cellulose esters, (e.g., ethyl cellulose, or cellulose acetate/butyrate), urethane-acrylate copolymers, and combinations thereof. Methods and materials for preparing aqueous emulsions or latexes of such polymers are well known, and many are widely available from commercial sources. In some embodiments, the non-fluorinated polymer is at least one of an acrylic polymer, a polyurethane, a polystyrene, or a styrene-acrylate copolymer.

In some embodiments, aqueous compositions comprising compounds according to the present disclosure may contain one or more water-miscible solvents (e.g., coalescing solvents) including ethers of polyhydric alcohols (e.g., ethylene glycol monomethyl (or monoethyl) ether, diethylene glycol methyl (or ethyl) ether, triethylene glycol monomethyl (or monoethyl) ether, 2-butoxyethanol (i.e., butyl cellusolve), or di(propylene glycol) methyl ether (DPM)); alkylene glycols and polyalkylene glycols (e.g., ethylene glycol, propylene glycol, butylene glycol, triethylene glycol, hexylene glycol, diethylene glycol, polyethylene glycol, polypropylene glycol); and 2,2,4-trimethyl-1,3-pentanediol monoisobutyrate (an ester alcohol available, for example, from Eastman Chemical Company, Kingsport, Tenn., under the trade designation "TEXANOL"). Other water-miscible organic solvents that may be added to a composition include alcohols having 1 to 4 carbon atoms (e.g., methanol, ethanol, isopropanol, or isobutanol); amides and lactams, (e.g., N,N-dimethylformamide, N,N-dimethylacetamide, or N-methylpyrrolidone); ketones and ketoalcohols (e.g., acetone, cyclohexanone, methyl isobutyl ketone, diacetone alcohol); ethers (e.g., tetrahydrofuran or dioxane); 1,3-dimethyl-2-imidazolidinone; and combinations thereof.

Depending on the application, aqueous compositions comprising compounds according to the present disclosure may also include at least one additive (e.g., biocides, fillers, additional leveling agents, emulsifiers, defoamers, anticorrosive agents, dispersants, and rust inhibitors). The aqueous compositions may also optionally contain at least one pigment.

When an aqueous composition comprising a non-fluorinated polymer and a compound according to the present disclosure is applied to a surface (e.g., in coating applications), water and solvent typically evaporate, and the polymer particles coalesce to form a continuous film. The aqueous composition can be applied to a surface, dried, and optionally heated, leaving the surface with a solid coating. The addition of compounds according to the present disclosure may improve the film forming properties of some compositions by improving the ability of the coating to wet the substrate and/or by allowing for even evaporation of the water (i.e., leveling) during film formation.

Aqueous compositions that may be improved by the addition of compounds according to the present disclosure include floor polishes and finishes, varnishes for a variety of substrates (e.g., wood floors), aqueous gels applied in the manufacture of photographic film, automotive or marine coatings (e.g., primers, base coats, or topcoats), sealers for porous substrates (e.g., wood, concrete, or natural stone), hard coats for plastic lenses, coatings for metallic substrates (e.g., cans, coils, electronic components, or signage), inks (e.g, for pens or gravure, screen, or thermal printing), and coatings used in the manufacture of electronic devices (e.g., photoresist inks). The aqueous compositions may be clear or pigmented.

In some embodiments, aqueous compositions comprising compounds according to some embodiments of the present disclosure and a non-fluorinated polymer may be useful as alkaline waterborne coating compositions, for example, amine-stabilized floor finish compositions. In some of these embodiments, the compound comprises at least one of a carboxylate, a sulfonate, a sulfate, phosphate, or a phosphonate group.

Methods comprising treating a surface according to the present disclosure can be carried out using a variety of application methods known to one of skill in the art (e.g., brushing, mopping, padding, bar coating, spraying (e.g., with a spray bottle), dip coating (i.e., immersing the substrate in a formulation), gravure coating, roll coating, spin-coating, flow coating, vacuum coating, painting, and wiping (e.g., with a sponge or cloth). When treating flat substrates of appropriate size, knife-coating or bar-coating may be used to ensure uniform coatings on a substrate.

In some embodiments of methods comprising treating a surface according to the present disclosure, the surface is a flooring surface comprising at least one of vinyl composition tiles, vinyl sheet flooring, linoleum, rubber sheeting, rubber tile, cork, synthetic sports flooring and vinyl asbestos tile, and non-resilient flooring substrates such as terrazzo, concrete, wood flooring, bamboo, wood laminate, engineered wood products (e.g., wood epoxy blends, permanently coated substrates such as those available from Pergo, Raleigh, N.C., under the trade designation "PERGO" and from DIAN, Gardena, Calif., under the trade designation "PARQUET BY DIAN"), stone, marble, slate, ceramic tile, grout, and dry shake flooring.

Compounds according to the present disclosure may also be useful as additives in cleaning solutions and may provide improved wetting of the surface and/or the contaminants to be removed. In some embodiments, methods comprising treating a surface according to the present disclosure include cleaning a surface. A cleaning solution is typically formulated to include about 0.001 to about 1 wt. %, or about 0.001 to about 0.5 wt. % of a compound according to the present disclosure, based on the total weight of the solution. For hard-surface cleaning, an aqueous solution comprising a compound according to the present disclosure is sprayed (e.g., from a spray bottle) or otherwise applied to a hard surface such as window glass, a mirror, or ceramic tile, and the surface is wiped clean with a paper or fabric wipe. The contaminated part may also be immersed or dipped into the aqueous solution. For methods of cleaning used in the manufacture of electronic materials, the cleaning solution is typically placed in a bath, and electronic parts are either dipped or run through the bath on a conveyor belt.

In some embodiments of composition comprising at least one of water or a water-miscible solvent and a compound according to the present disclosure, the composition further comprises at least one gas (i.e., the composition is a foam).

In some embodiments of compounds according to the present disclosure, X is alkylene having at least 10 (e.g., at least 12, 15, 18, 20, 22, 25, 28, or 30) carbon atoms. These compounds may be useful, for example, to reduce the surface tension of compositions containing hydrocarbon solvents. Suitable hydrocarbon solvents include crude oil; refined hydrocarbons (e.g., gasoline, kerosene, and diesel); paraffinic and isoparaffinic hydrocarbons (e.g., pentanes, hexanes, heptanes, higher alkanes, and isoparaffinic solvents obtained from Total Fina, Paris, France, under trade designations "ISANE IP 130" and "ISANE IP 175" and from Exxon Mobil Chemicals, Houston, Tex., under the trade designation "ISOPAR"); mineral oil; ligroin; naphthenes; aromatics (e.g., xylenes and toluene); natural gas condensates; and combinations (either miscible or immiscible) thereof. In some embodiments, compositions comprising a hydrocarbon solvent and a compound according to the present disclosure further comprise at least one gas (i.e., the composition is a foam).

Typically, compositions (e.g., aqueous or hydrocarbon foams) according to and/or prepared by the present disclosure include from at least 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.5, 1, 1.5, 2, 3, 4, or 5 percent by weight, up to 5, 6, 7, 8, 9, or 10 percent by weight of at least one compound according to the present disclosure, based on the total weight of the composition. For example, the amount of a compound according to the present disclosure in a foam may be in a range of from 0.01 to 10, 0.1 to 10, 0.1 to 5, 1 to 10, or from 1 to 5 percent by weight, based on the total weight of the composition. Lower and higher amounts of the compound in the composition (e.g., a foam) may also be used, and may be desirable for some applications.

Forming gas bubbles (e.g., nitrogen, carbon dioxide, and air) in a composition comprising a liquid (e.g., water or a solvent) and a compound according to the present disclosure can be carried out using a variety of mechanisms (e.g., mechanical and chemical mechanisms). Useful mechanical foaming mechanisms include agitating (e.g., shaking, stirring, and whipping) the composition, injecting gas into the composition (e.g., inserting a nozzle beneath the surface of the composition and blowing gas into the formulation) and combinations thereof. Useful chemical foaming mechanisms include producing gas in situ through a chemical reaction, decomposition of a component of the composition (e.g., a component that liberates gas upon thermal decomposition), evaporating a component of the composition (e.g., a liquid gas, and volatilizing a gas in the composition by decreasing the pressure on the composition or heating the composition). Foams according to and/or prepared by methods according to the present disclosure comprise gas bubbles at volume fractions ranging from 10% to 90% of the total foam volume.

Compounds according to the present disclosure may be useful additives, for example, in foams for delivering oil- and/or water-repellent treatments to substrates (including fibrous substrates, e.g., textile, non-woven, carpet, and leather).

In some embodiments, compounds according to the present disclosure may provide repellent properties to a variety of surfaces and improve the ability to clean these surfaces. Articles according to the present disclosure, having a surface treated with a compound according to the present disclosure may be at least one of non-staining, stain-releasing with simple washing methods, oil resistant (e.g., resistant to fingerprints), resistant to lime deposits, or resist being worn-off due to wear and abrasion from use, cleaning, and the elements. In some of these embodiments, Z is a phosphate or phosphonate group.

In any of the aforementioned embodiments of compounds according to and/or useful in practicing the present disclosure (e.g., coating or cleaning solution compositions and foams), compounds according to the present disclosure can be used individually or in combination with a non-fluorinated surfactant (e.g., a hydrocarbon or silicone surfactant) to produce the desired surface tension reduction or wetting improvement. Useful auxiliary surfactants may be found, for example, in Industrial Applications Of Surfactants, D. R. Karsa, Ed., Royal Society of Chemistry, London, and M. Rosen, Surfactants and Interfacial Phenomena, Wiley-Interscience, New York.

The compounds disclosed herein, which have partially fluorinated polyether groups and/or have fully fluorinated polyether groups with a low number (e.g., up to 4) continuous perfluorinated carbon atoms, are herein demonstrated to have useful surfactant properties and may provide a lower-cost alternative to surfactants having a larger number of continuous perfluorinated carbon atoms. The compounds disclosed herein may be useful, for example, as nonionic, anionic, cationic, or zwitterionic surfactants. For some applications that require rapid spraying and wetting processes (e.g., painting of car bodies, metal working, paper making, and textile manufacturing), it is advantageous to use highly dynamic surfactants that can reduce the surface tension within milliseconds. In some embodiments, the present disclosure provides dynamic surfactants (e.g., compounds represented by formula [Rf—C(O)O$^-$ $^+$NH(R')—X]$_2$—NH(R)$^+$RfC(O)O$^-$ or Rf—C(O)O$^-$ $^+$NH(R')—X—NH(R)$_2$$^+$RfC(O)O$^-$) that rival the performance of the best known dynamic surfactants (see, e.g., U.S. Pat. No. 5,503,967 column 21, line 10 and the perfluoropolyether salts in U.S. Pat. Nos. 5,453,539 and 5,536,425).

Compounds according to the present disclosure reduce the surface tension of a liquid with which they are combined. In some embodiments, the surface tension of the liquid is reduced by at least 10% (in some embodiments, at least 20%, 30%, 40%, 50%, 60%, or even 70%). In some embodiments, the surface tension of the liquid is reduced to an extent not less than when an equivalent liquid is combined with an amount of a surfactant, wherein the surfactant is the same as the compound except Rf is replaced with a group represented by formula $C_3F_7$—O—$CF(CF_3)$—, and wherein the amount by weight of the surfactant is the same as the amount by weight of the compound. The term "equivalent liquid" refers to a liquid that is the same in all respects except for the identity of the surfactant.

Embodiments of this disclosure are further illustrated by the following non-limiting examples, but the particular materials and amounts thereof recited in these examples, as well as other conditions and, details, should not be construed to unduly limit this disclosure.

EXAMPLES

In the following examples, all reagents were obtained from Sigma-Aldrich, St. Louis, Mo. or Bornem, Belgium unless indicated otherwise. All percentages and ratios reported are by weight unless indicated otherwise.

Example 1

Part A

The methyl ester of perfluoro-3,7-dioxaoctanoic acid ($CF_3OCF_2CF_2CF_2OCF_2C(O)OCH_3$) was prepared according to the method described in U.S. Pat. App. Pub. No. 2007/0015864 (Hintzer et al.) in the Preparation of Compound 1, the disclosure of which preparation is incorporated herein by reference.

Part B

In a three-necked 100-mL flask fitted with a stirrer, thermometer, and condenser were placed 18 grams (0.05 mole) of the methyl ester from Part A and dimethylaminopropylamine (DMAPA) (5.1 grams, 0.05 mole). The reaction mixture was heated under nitrogen at 50° C. using a heating mantle for three hours. Methanol was then removed under reduced pressure. Acetic acid (3 grams, 0.05 mole) was added, and the resulting mixture was stirred for two hours under nitrogen at 30° C. A clear, yellow, slightly viscous liquid was obtained, which was identified to be $CF_3OCF_2CF_2CF_2OCF_2C(O)NHCH_2CH_2CH_2N^+(CH_3)_2H^-OC(O)CH_3$ using proton and $^{19}$fluorine nuclear magnetic resonance (NMR) spectroscopy.

Example 2

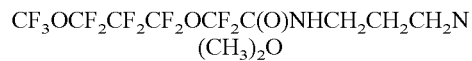

In a three-necked 100-mL flask fitted with a stirrer, thermometer, and condenser were placed 18 grams (0.05 mole) of the methyl ester from Example 1, Part A and DMAPA (5.1 grams, 0.05 mole). The reaction mixture was heated under nitrogen at 50° C. using a heating mantle for three hours. Methanol was then removed under reduced pressure. Ethanol (24 grams) and 8.4 grams (0.075 mole) of 30% hydrogen peroxide in water were added, and the mixture was heated at 70° C. for six hours. A clear, slightly amber solution of $CF_3OCF_2CF_2CF_2OCF_2C(O)NHCH_2CH_2CH_2N(CH_3)_2O$ was obtained.

Example 3

$CF_3OCF_2CF_2CF_2OCHFCF_2C(O)NHCH_2CH_2CH_2N^+(CH_3)_2H^-OC(O)CH_3$

Part A

The methyl ester of 3-H-perfluoro-4,8-dioxanonanoic acid ($CF_3O(CF_2)_3OCHFCF_2COOCH_3$) was prepared according to the method described in the synthesis of compound 2 in U.S. Pat. App. Pub. No. 2007/0142541 (Hintzer et al.); the disclosure of this synthesis is incorporated herein by reference.

Part B

The method of Part B of Example 1 was followed except using 19.6 grams of $CF_3O(CF_2)_3OCHFCF_2COOCH_3$ instead of $CF_3OCF_2CF_2CF_2OCF_2C(O)OCH_3$.

Example 4

$CF_3OCF_2CF_2CF_2OCHFCF_2C(O)NHCH_2CH_2CH_2N(CH_3)_2O$

The method of Example 2 was followed except using 19.6 grams of $CF_3O(CF_2)_3OCHFCF_2COOCH_3$, prepared as described in Part A of Example 3, instead of $CF_3OCF_2CF_2CF_2OCF_2C(O)OCH_3$.

Example 5

$CF_3CF_2CF_2OCHFCF_2C(O)NHCH_2CH_2CH_2N^+(CH_3)_2H^-OC(O)CH_3$

Part A

The methyl ester of 3-H-perfluoro-4-oxaheptanoic acid ($C_3F_7OCHFCF_2COOCH_3$) was prepared according to the method described in the synthesis of compound 4 in U.S. Pat. App. Pub. No. 2007/0142541 (Hintzer et al.); the disclosure of this synthesis is incorporated herein by reference.

Part B

The method of Part B of Example 1 was followed except using 16.3 grams of $CF_3CF_2CF_2OCHFCF_2COOCH_3$ instead of $CF_3OCF_2CF_2CF_2OCF_2C(O)OCH_3$.

Example 6

$CF_3CF_2CF_2OCHFCF_2C(O)NHCH_2CH_2CH_2N(CH_3)_2O$

The method of Example 2 was followed except using 16.3 grams of $CF_3CF_2CF_2OCHFCF_2COOCH_3$, prepared as described in Part A of Example 5, instead of $CF_3OCF_2CF_2CF_2OCF_2C(O)OCH_3$.

Example 7

$CF_3OCF_2OCF_2OCF_2C(O)NHCH_2CH_2CH_2N^+(CH_3)_2H^-OC(O)CH_3$

Part A

The methyl ester of perfluoro-3,5,7-trioxaoctanoic acid (obtained from Anles Ltd., St. Petersburg, Russia) was prepared by esterification in methanol using 50% aqueous sulfuric acid. Flash distillation of the reaction mixture resulted in a two-phase distillate. The lower phase was fractionally distilled to provide $CF_3OCF_2OCF_2OCF_2COOCH_3$.

Part B

The method of Part B of Example 1 was followed except using 16.4 grams of $CF_3OCF_2OCF_2OCF_2COOCH_3$ instead of $CF_3OCF_2CF_2CF_2OCF_2C(O)OCH_3$.

Example 8

$CF_3OCF_2OCF_2OCF_2C(O)NHCH_2CH_2CH_2N(CH_3)_2O$

The method of Example 2 was followed except using 16.4 grams of $CF_3OCF_2OCF_2OCF_2COOCH_3$, prepared as described in Part A of Example 7, instead of $CF_3OCF_2CF_2CF_2OCF_2C(O)OCH_3$.

Example 9

$CF_3OCF_2OCF_2OCF_2OCF_2C(O)NHCH_2CH_2CH_2N^+(CH_3)_2H^-OC(O)CH_3$

Part A

The methyl ester of perfluoro-3,5,7,9-tetraoxadecanoic acid (obtained from Anles Ltd., St. Petersburg, Russia) was prepared by esterification in methanol using 50% aqueous sulfuric acid. Flash distillation of the reaction mixture resulted in a two-phase distillate. The lower phase was fractionally distilled to provide $CF_3OCF_2OCF_2OCF_2OCF_2COOCH_3$.

Part B

The method of Part B of Example 1 was followed except using 19.6 grams of $CF_3OCF_2OCF_2OCF_2OCF_2COOCH_3$ instead of $CF_3OCF_2CF_2CF_2OCF_2C(O)OCH_3$.

Example 10

$CF_3OCF_2OCF_2OCF_2OCF_2C(O)NHCH_2CH_2CH_2N(CH_3)_2O$

The method of Example 2 was followed except using 19.6 grams of $CF_3OCF_2OCF_2OCF_2OCF_2COOCH_3$, prepared as described in Part A of Example 9, instead of $CF_3OCF_2CF_2CF_2OCF_2C(O)OCH_3$.

Example 11

$CF_3OCF_2CF_2CF_2OCHFC(O)NHCH_2CH_2CH_2N^+(CH_3)_2H^-OC(O)CH_3$

Part A

The methyl ester of 2-H-perfluoro-3,7-dioxaoctanoic acid ($CF_3OCF_2CF_2CF_2OCHFCOOCH_3$) was prepared according to the method described in the synthesis of compound 3 (paragraph [0062]) in U.S. Pat. App. Pub. No. 2007/0142541 (Hintzer et al.); the disclosure of this synthesis is incorporated herein by reference.

Part B

The method of Part B of Example 1 was followed except using 18 grams of $CF_3OCF_2CF_2CF_2OCHFCOOCH_3$ instead of $CF_3OCF_2CF_2CF_2OCF_2C(O)OCH_3$.

Example 12

$CF_3OCF_2CF_2CF_2OCHFC(O)NHCH_2CH_2CH_2N(CH_3)_2O$

The method of Example 2 was followed except using 18 grams of $CF_3OCF_2CF_2CF_2OCHFCOOCH_3$, prepared as described in Part A of Example 11, instead of $CF_3OCF_2CF_2CF_2OCF_2C(O)OCH_3$.

Example 13

$CF_3CF_2CF_2OCHFC(O)NHCH_2CH_2CH_2N^+(CH_3)_2H^-OC(O)CH_3$

Part A
The methyl ester of 2-H-perfluoro-3-oxahexanoic acid ($CF_3CF_2CF_2OCHFCOOCH_3$) was prepared according to the method described in the synthesis of compound 5 in U.S. Pat. App. Pub. No. 2007/0142541 (Hintzer et al.); the disclosure of this synthesis is incorporated herein by reference.
Part B
The method of Part B of Example 1 was followed except using 13.8 grams of $CF_3CF_2CF_2OCHFCOOCH_3$ instead of $CF_3OCF_2CF_2CF_2OCF_2C(O)OCH_3$.

Example 14

$CF_3CF_2CF_2OCHFC(O)NHCH_2CH_2CH_2N(CH_3)_2O$

The method of Example 2 was followed except using 13.8 grams of $CF_3CF_2CF_2OCHFCOOCH_3$, prepared as described in Part A of Example 13, instead of $CF_3OCF_2CF_2CF_2OCF_2C(O)OCH_3$.

Example 15

$CF_3OCF_2OCF_2OCF_2OCF_2C(O)NHCH_2CH_2CH_2N^+(CH_3)_2CH_2CH_2CH_2SO_3^-$

In a three-necked 100-mL flask, fitted with a stirrer, thermometer, and condenser were placed 19.6 grams (0.05 mole) of $CF_3OCF_2OCF_2OCF_2OCF_2COOCH_3$, prepared as described in Part A of Example 9, and DMAPA (5.1 grams, 0.05 mole). The reaction mixture was heated under a nitrogen atmosphere for three hours at 50° C. using a heating mantle. Methanol was then removed under reduced pressure. 1,3-Propanesultone (6.1 grams, 0.05 mole) was added, resulting in an exothermic reaction. The reaction mixture was further heated at 50° C. for three hours, and 15 grams ethanol and 15 grams of deionized water were added. A clear, amber solution of $CF_3OCF_2OCF_2OCF_2OCF_2C(O)NHCH_2CH_2CH_2N^+(CH_3)_2CH_2CH_2CH_2SO_3^-$ was obtained.

Example 16

$CF_3OCF_2CF_2CF_2OCHFCF_2C(O)NHCH_2CH_2CH_2N^+(CH_3)_2CH_2CH_2CH_2SO_3^-$

The method of Example 15 was followed except using 19.6 grams of $CF_3O(CF_2)_3OCHFCF_2COOCH_3$, prepared as described in Part A of Example 3, instead of $CF_3OCF_2OCF_2OCF_2OCF_2COOCH_3$.

Example 17

$CF_3OCF_2CF_2CF_2OCF_2C(O)O(CH_2CH_2O)_nH$

In a three-necked 100-mL flask, fitted with a stirrer, heating mantle, dry ice condenser, and thermometer, were placed 17.3 grams (0.05 mole) $CF_3OCF_2CF_2CF_2OCF_2C(O)OH$, which was heated to 80° C. Ethylene oxide (2.2 grams, 0.05 mole) was added, and the reaction mixture was heated until no more condensation drops of ethylene oxide were observed. The mixture was cooled to 30° C. under nitrogen and then 0.2 gram boron trifluoride diethyl etherate was added. The mixture was heated to 80° C., and additional ethylene oxide (8.8 grams, 0.2 mole) was added over about 30 minutes at a rate sufficient to maintain a gentle reflux of ethylene oxide. The heating was continued for three hours after the addition until refluxing was no longer observed. The reaction mixture was then concentrated under reduced pressure at 80° C. to provide a brown liquid.

$CF_3OCF_2CF_2CF_2OCF_2C(O)OH$ was prepared from $CF_3OCF_2CF_2CF_2OCF_2C(O)ONH_4$, which was prepared according to the method described in U.S. Pat. App. Pub. No. 2007/0015864 (Hintzer et al.) in the Preparation of Compound 1, the disclosure of which preparation is incorporated herein by reference. The ammonium salt was treated with sulfuric acid, and the lower phase was separated and distilled.

Example 18

$CF_3OCF_2OCF_2OCF_2OCF_2C(O)O(CH_2CH_2O)_nH$

The method of Example 17 was followed except using 18.9 grams of perfluoro-3,5,7,9-tetraoxadecanoic acid (obtained from Anles Ltd., St. Petersburg, Russia) instead of $CF_3OCF_2CF_2CF_2OCF_2C(O)OH$.

Example 19

$CF_3OCF_2CF_2CF_2OCF_2C(O)N(CH_3)CH_2C(O)O—K+$

In a three-necked 100-mL flask fitted with a stirrer, thermometer, and condenser were placed 18 grams (0.05 mole) of $CF_3OCF_2CF_2CF_2OCF_2C(O)OCH_3$, prepared in Example 1, Part A, and dry sarcosine (4.5 grams, 0.05 mole). The reaction mixture was heated under nitrogen at 60° C. using a heating mantle for 48 hours and then cooled to about 30° C. Isopropanol (23 grams) and potassium hydroxide (2.8 grams, 0.05 mole) were added to provide a solution of $CF_3OCF_2CF_2CF_2OCF_2C(O)N(CH_3)CH_2C(O)O—K+$.

Example 20

$CF_3OCF_2OCF_2OCF_2OCF_2C(O)N(CH_3)CH_2C(O)O—K+$

The method of Example 19 was followed except using 19.6 grams of $CF_3OCF_2OCF_2OCF_2OCF_2COOCH_3$, prepared as described in Part A of Example 9, instead of $CF_3OCF_2CF_2CF_2OCF_2C(O)OCH_3$.

Example 21

$CF_3OCF_2CF_2CF_2OCF_2C(O)NHCH_2CH_2OC(O)CH_2P(O)(OH)_2$

Part A
$CF_3OCF_2CF_2CF_2OCF_2C(O)OCH_3$, prepared in Example 1, Part A, was treated with ethanolamine according to the method described on column 16, lines 37-62 of U.S. Pat. No. 7,094,829 (Audenaert et al.), the disclosure of which method is incorporated herein by reference.
Part B
In a three-necked 100-mL flask fitted with a stirrer, thermometer, condenser, and Dean-Stark trap were placed 3.9 grams (0.01 mole) of the material from Part A, 2-phosphonoacetic acid (1.4 gram, 0.01 mole), methyl isobutyl ketone (26 grams), and methanesulfonic acid (0.05 gram). The reaction mixture was heated at reflux for about six hours. Throughout the course of the reaction, about 0.2 gram of water was collected in the Dean-Stark trap. $CF_3OCF_2CF_2CF_2OCF_2C(O)NHCH_2CH_2OC(O)CH_2P(O)O(OH)_2$ was obtained as a brown liquid solution in methyl isobutyl ketone.

Example 22

$CF_3OCF_2OCF_2OCF_2OCF_2C(O)NHCH_2CH_2OC(O)CH_2P(O)(OH)_2$

Example 22 was prepared using the method of Example 21 except using the methyl ester described in Part A of Example 9 in Part A and using 4.2 grams of $CF_3OCF_2OCF_2OCF_2OCF_2C(O)NHCH_2CH_2OH$ instead of $CF_3OCF_2CF_2CF_2OCF_2C(O)NHCH_2CH_2OH$ in Part B of Example 21.

Comparative Example A

The method of Part B of Example 1 was followed except using 16.3 grams of $CF_3CF_2CF_2OCF(CF_3)COOCH_3$ (obtained from Hoechst AG, Germany) instead of $CF_3OCF_2CF_2CF_2OCF_2C(O)OCH_3$.

Comparative Example B

The method of Example 2 was followed except using 16.3 grams of $CF_3CF_2CF_2OCF(CF_3)COOCH_3$ (obtained from Hoechst AG, Germany) instead of $CF_3OCF_2CF_2CF_2OCF_2C(O)OCH_3$.

Comparative Example C

Perfluorohexanoic acid (obtained from ABCS GmBh Germany) (3.1 grams, 0.01 mole) was neutralized with potassium hydroxide (0.6 gram, 0.01 mole) in 5 grams of deionized water and 5 grams of isopropanol. A clear solution resulted after 30 minutes stirring at room temperature.

Surface Tension Measurement

Examples 1 to 20 were diluted with deionized water to the concentrations given in Table 1 (below). Surface tensions were measured for the solutions containing Examples 1 to 20 using a Kruss K-12 tensiometer (obtained from Kruss GmbH, Hamburg, Germany) using the Du Nouy ring method at 20° C. The results are summarized in Table 1 (below).

TABLE 1

| Example | Concentration (ppm) | Surface tension (mN/m) |
|---|---|---|
| 1 | 1000 | 18.7 |
|  | 500 | 24.1 |
|  | 100 | 39.6 |
|  | 10 | 59.1 |
| 2 | 1000 | 18.7 |
|  | 500 | 25.8 |
|  | 100 | 42.8 |
|  | 10 | 59.2 |
| 3 | 1000 | 17.7 |
|  | 500 | 24.6 |
|  | 100 | 41.1 |
|  | 10 | 56.8 |
| 4 | 1000 | 20.5 |
|  | 100 | 39.9 |
|  | 10 | 56.1 |
| 5 | 1000 | 39.3 |
|  | 100 | 58.7 |
|  | 10 | 66.3 |

TABLE 1-continued

| Example | Concentration (ppm) | Surface tension (mN/m) |
|---|---|---|
| 6 | 1000 | 41.1 |
|  | 100 | 59.4 |
|  | 10 | 66.9 |
| 7 | 1000 | 26.5 |
|  | 100 | 43.4 |
|  | 10 | 55.9 |
| 8 | 1000 | 23.8 |
|  | 100 | 40.2 |
|  | 10 | 52.7 |
| 9 | 1000 | 17.8 |
|  | 500 | 18.0 |
|  | 100 | 38.6 |
|  | 10 | 59.1 |
| 10 | 1000 | 18.1 |
|  | 500 | 18.5 |
|  | 100 | 35.7 |
|  | 10 | 55.4 |
| 11 | 1000 | 20.7 |
|  | 100 | 38.7 |
|  | 10 | 57.4 |
| 12 | 1000 | 19.2 |
|  | 100 | 35.5 |
|  | 10 | 60.0 |
| 13 | 1000 | 36.8 |
|  | 100 | 55.1 |
|  | 10 | 64.7 |
| 14 | 1000 | 38.3 |
|  | 100 | 59.1 |
|  | 10 | 66.2 |
| 15 | 1000 | 18.3 |
|  | 500 | 18.7 |
|  | 100 | 33.9 |
|  | 10 | 56.8 |
| 16 | 1000 | 20.2 |
|  | 500 | 21.0 |
|  | 100 | 40.3 |
|  | 10 | 56.5 |
| 17 | 1000 | 20.6 |
|  | 100 | 35.3 |
|  | 10 | 57.6 |
| 18 | 1000 | 20.1 |
|  | 100 | 34.8 |
|  | 10 | 58.0 |
| 19 | 1000 | 19.5 |
|  | 100 | 36.6 |
|  | 10 | 57.2 |
| 20 | 1000 | 19.2 |
|  | 100 | 38.4 |
|  | 10 | 55.3 |
| Comp. Ex. A | 1000 | 20.2 |
|  | 100 | 37.4 |
|  | 10 | 64.8 |
| Comp. Ex. B | 1000 | 19.7 |
|  | 100 | 42.1 |
|  | 10 | 60.9 |
| Comp. Ex. C | 1000 | 58.5 |

Dynamic Contact Angle on Glass

Dynamic advancing and receding contact angles were measured on flat glass (obtained from Aqua Production, France) using a Kruss DSA 100 (obtained from Kruss GmbH). Examples 21 and 22 were diluted to 20% solids in methyl isobutyl ketone. They were applied with a K Hand Coater Bar nr 3 (obtained from RK Print Coat Ltd, UK) at room temperature, leaving a 24 micron wet film deposited, and the coatings were dried at room temperature. The advancing and receding contact angles were measured after 1 hour at room temperature. For the purposes of comparison, a fluorochemical polymeric glass coating was obtained from 3M Company, St. Paul, Minn., under the trade designation "ECC-4000" and was used as Comparative Example D (Comp. Ex. D). Comp. Ex. D was spray applied at 0.1% concentration. The results are summarized in Table 2 (below).

TABLE 2

| Example | Advancing/Receding CA with water | Advancing/Receding CA with hexadecane |
|---|---|---|
| Example 21 | 110/80 | 77/58 |
| Example 22 | 108/93 | 72/40 |
| Comp. Ex. D "ECC-4000" | 113/95 | 71/61 |

Example 23

$(CF_3CFH-O-(CF_2)_5CH_2O)_2P(O)O^{-+}NH_4$

Part A $CF_3CFH-O-(CF_2)_5COOH$ (426 grams, 1.0 mole), which was prepared according to the method described in Example 3 of U.S. Pat. App. Pub. No. 2007/0276103, was esterified at 65° C. with methanol (200 grams, 6.3 moles) and concentrated sulfuric acid (200 grams, 2.0 moles). The reaction mixture was washed with water and distilled at 172° C. to give 383 grams of $CF_3CFH-O-(CF_2)_5COOCH_3$, which was combined with material from a repeat run and used in Part B.

Part B

A 5-L round-bottom flask equipped with a mechanical stirrer and nitrogen bubbler was charged with 1 L of 1,2-dimethoxyethane and sodium borohydride (76 grams, 2.0 moles) and heated to 80° C. $CF_3CFH-O-(CF_2)_5COOCH_3$ (713 grams, 1.67 mole), prepared as described in Part A, was added to the stirred slurry over a period of one hour. A mixture of concentrated sulfuric acid (198 grams) and water (1.0 L) was added to the reaction mixture. The lower phase was separated, and the solvent was removed by distillation. Further distillation provided 506 grams of $CF_3CFH-O-(CF_2)_5CH_2OH$ (boiling point 173° C.), the structure of which was confirmed by Fourier Transform Infrared Spectroscopy (FTIR) and $^1H$ and $^{19}F$ Nuclear Magnetic Resonance (NMR) Spectroscopy.

Part C

A 100-mL three-necked flask equipped with a magnetic stir bar, thermometer, and a cooling water condenser connected to nitrogen was charged with phosphorous (V) oxychloride (3.1 grams, 20 mmol) and six grams of toluene. The solution was cooled to 0° C. with an ice-water bath, and water (0.36 gram, 20 mmol) was added to the solution slowly with a syringe while maintaining the temperature below 5° C. The reaction mixture was stirred at about 0° C. for one hour. Then a solution of a portion of the material from Part B (15.9 grams, 0.040 mole) in 16 grams of toluene was added. The solution was heated at 110° C. for 24 hours and then allowed to cool to room temperature. The solvent was removed under reduced pressure.

Part D

A portion of the material from Part C (2.5 grams) was diluted with 7.5 grams of water, and the pH was adjusted to about 9 using 5% aqueous ammonia. The resulting solution was diluted with isopropyl alcohol to 150 grams total to provide a 2% by weight solution.

Example 24

$(CF_3CFH-O-(CF_2)_3CH_2O)_2P(O)O^{-+}NH_4$

Part A $FC(O)CF(CF_3)-O-(CF_2)_3COF$ (503 grams, 1.4 mole), prepared as described in U.S. Pat. App. Pub. No. 2004/0116742, was added over a period of two hours to a stirred mixture of sodium carbonate (387 grams, 3.7 moles) and diglyme (650 grams) at 78° C. The reaction liberated carbon dioxide gas. Distilled water (35 grams, 1.9 mole) was added at 85° C., and then the reaction mixture was heated to 165° C. and maintained at that temperature for 30 minutes. The reaction was allowed to cool, and sulfuric acid (250 grams, 2.6 moles) in 1250 grams of water was added. Two layers formed, and the top layer was washed with 33% sulfuric acid and then esterified at 65° C. with methanol (200 grams, 6.3 moles) and concentrated sulfuric acid (200 grams, 2.0 moles). The reaction mixture was washed with water and distilled at 52° C. at 15 mmHg ($2.0 \times 10^3$ Pa) to give 258 grams of $CF_3CFH-O-(CF_2)_3COOCH_3$.

Part B $CF_3-CFH-O-(CF_2)_3-CH_2-OH$ was prepared according to the method of Example 23, Part B, except 200 grams (0.6 mole) of $CF_3-CFH-O-(CF_2)_3-C(O)O-CH_3$ was reduced with 30 grams (0.79 mole) of sodium borohydride in 0.2 L of 1,2-dimethoxyethane. At the end of the reaction 150 grams of concentrated sulfuric acid in 0.3 L of water were added, and 115 grams of $CF_3-CFH-O-(CF_2)_3-CH_2-OH$, having a boiling point of 130° C., were obtained.

Part C $(CF_3CFH-O-(CF_2)_3CH_2O)_2P(O)O^{-+}NH_4$ was prepared according to the methods of Example 23, Parts C and D, except five grams of toluene were used, and a solution of the material from Part B (12.7 grams, 40 mmol) in 13 grams of toluene were added. After cooling to room temperature, the solvent was removed under reduced pressure to give 11.6 grams of liquid. A portion of the liquid (3 grams) was diluted with 7 grams of water, and the pH was adjusted to about 9 with 5% aqueous ammonia. The resulting solution was diluted with isopropyl alcohol to 150 grams total to provide a 2% by weight solution.

Surface Tension Measurement

Surface tension was determined for Examples 23 to 24 using a Kruss K12 Tensiometer, purchased from Kruss USA, Charlotte, N.C. For each Example the 2% solution in isopropanol/water was added dropwise to water, and the surface tension of the resulting solution was measured at room temperature. The results are shown in Table 3, below.

TABLE 3

| Example | Concentration (ppm) | Surface tension (mN/m) |
|---|---|---|
| 23 | 1400 | 18 |
|  | 71 | 29 |
| 24 | 1400 | 19 |
|  | 71 | 38 |

Example 25

$(CF_3OCF_2OCF_2OCF_2C(O)O^-)_2\ ^+NH_3$
$CH_2CH_2CH_2N^+(CH_3)_2$

Perfluoro-3,5,7-trioxaoctanoic acid (31.2 grams, 0.1 mole), obtained from Anles Ltd., and 31 grams of ethanol were added to a 250-mL three-necked flask fitted with a stirrer, a thermometer, and a condenser, and 5.1 grams (0.05 mole) of DMAPA was added dropwise with stirring over a period of about 15 minutes. The reaction mixture was stirred for about two hours after the addition at room temperature to provide a clear, slightly yellow solution of $(CF_3OCF_2OCF_2OCF_2C(O)O^-)_2$ $^+NH_3CH_2CH_2CH_2N^+(CH_3)_2$.

Example 26

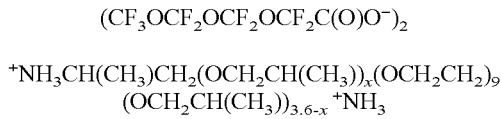

Example 26 was prepared according to the method of Example 25 except 30 grams of a polyetheramine obtained from Huntsman Corporation, The Woodlands, Tex., under the trade designation "JEFFAMINE ED-600" were used instead of DMAPA.

Example 27

Example 27 was prepared according to the method of Example 25 except 37.8 grams of perfluoro-3,5,7,9-tetraoxadecanoic acid (obtained from Anles Ltd.) were used instead of perfluoro-3,5,7-trioxaoctanoic acid.

Example 28

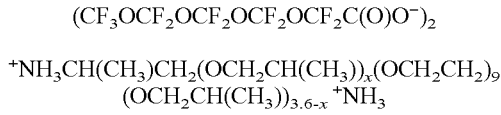

Example 28 was prepared according to the method of Example 25 except 37.8 grams of perfluoro-3,5,7,9-tetraoxadecanoic acid (obtained from Anles Ltd.) were used instead of perfluoro-3,5,7-trioxaoctanoic acid, and 30 grams of a polyetheramine obtained from Huntsman Corporation under the trade designation "JEFFAMINE ED-600" were used instead of DMAPA.

Example 29

$CF_3OCF_2OCF_2OCF_2C(O)O^-$ $^+NH_3CH_2CH_2CH_2N(CH_3)_2$

Example 29 was prepared according to the method of Example 25 except 10.2 grams (0.1 mole) of DMAPA were used.

Example 30

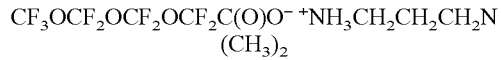

Example 30 was prepared according to the method of Example 25 except 3.4 grams (0.03 mole) of diethylenetriamine were used instead of DMAPA.

Example 31

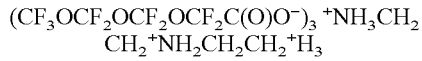

Example 31 was prepared according to the method of Example 25 except 37.8 grams of perfluoro-3,5,7,9-tetraoxadecanoic acid (obtained from Anles Ltd.) were used instead of perfluoro-3,5,7-trioxaoctanoic acid, and 10.2 grams (0.1 mole) of DMAPA were used.

Example 32

Example 32 was prepared according to the method of Example 25 except 37.8 grams of perfluoro-3,5,7,9-tetraoxadecanoic acid (obtained from Anles Ltd.) were used instead of perfluoro-3,5,7-trioxaoctanoic acid, and 3.4 grams (0.03 mole) of diethylenetriamine were used instead of DMAPA.

Example 33

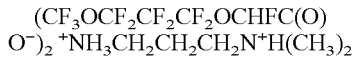

Example 33 was prepared according to the method of Example 25 except 34.1 grams of 2-H-perfluoro-3,7-dioxaoctanoic acid were used instead of perfluoro-3,5,7-trioxaoctanoic acid.

2-H-Perfluoro-3,7-dioxaoctanoic acid was prepared was prepared from $CF_3OCF_2CF_2CF_2OCHFC(O)ONH_4$, which was prepared according to the method described in U.S. Pat. App. Pub. No. 2007/0015864 (Hintzer et al.) in the Preparation of Compound 12, the disclosure of which preparation is incorporated herein by reference. The ammonium salt was treated with sulfuric acid, and the lower phase was separated and distilled.

Example 34

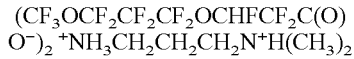

Example 34 was prepared according to the method of Example 25 except 39.2 grams of 3-H-perfluoro-4,8-dioxanonanoic acid were used instead of perfluoro-3,5,7-trioxaoctanoic acid.

3-H-Perfluoro-4,8-dioxanonanoic acid was prepared was prepared from $CF_3OCF_2CF_2CF_2OCHFCF_2C(O)ONH_4$, which was prepared according to the method described in U.S. Pat. App. Pub. No. 2007/0015864 (Hintzer et al.) in the Preparation of Compound 11, the disclosure of which preparation is incorporated herein by reference. The ammonium salt was treated with sulfuric acid, and the lower phase was separated and distilled.

Dynamic Surface Tension Measurement

Examples 25 to 34 were diluted with deionized water to the concentrations given in Table 4 (below). Surface tensions were measured for the solutions containing Examples 25 to 34 using a Kruss tensiometer (obtained from Kruss GmbH under the trade designation "KRUSS BUBBLE PRESSURE TENSIOMETER BP2") using the maximum bubble pressure technique and different surface ages at 22° C. The results are summarized in Table 4 (below) for a surface age of 100 milliseconds.

TABLE 4

| Example | Concentration (ppm) | Surface tension (mN/m) |
|---------|---------------------|------------------------|
| 25      | 5000                | 19.8                   |
|         | 1000                | 39.4                   |
|         | 500                 | 51.3                   |

TABLE 4-continued

| Example | Concentration (ppm) | Surface tension (mN/m) |
|---------|---------------------|------------------------|
| 26 | 5000 | 34.5 |
|    | 1000 | 49.0 |
|    | 500  | 55.5 |
| 27 | 5000 | 19.5 |
|    | 1000 | 39.9 |
|    | 500  | 50.2 |
| 28 | 5000 | 25.5 |
|    | 1000 | 38.4 |
|    | 500  | 48.0 |
| 29 | 5000 | 38.7 |
|    | 1000 | 58.8 |
|    | 500  | 65.2 |
| 30 | 5000 | 29.9 |
|    | 1000 | 53.5 |
|    | 500  | 60.0 |
| 31 | 5000 | 22.2 |
|    | 1000 | 45.1 |
|    | 500  | 56.3 |
| 32 | 500  | Insoluble |
| 33 | 5000 | 24.1 |
|    | 1000 | 42.4 |
|    | 500  | 57.5 |
| 34 | 5000 | 20.0 |
|    | 1000 | 39.2 |
|    | 500  | 50.8 |

Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A compound represented by formula:

$(Rf-Q-X)_s—Z$;

wherein
Rf is selected from the group consisting of:
    $Rf^a—(O)_r—CHF—(CF_2)_n—$;
    $[Rf^b—(O)_t—C(L)H—CF_2—O]_m—W—$;
    $CF_3CFH—O—(CF_2)_p—$;
    $CF_3—(O—CF_2)_z—$; and
    $CF_3—O—(CF_2)_3—O—CF_2—$;
Q is selected from the group consisting of —C(O)O$^-$ $^+$NH(R')$_2$—, —C(O)—N(R')—, and —C(O)—O—, wherein R' is selected from the group consisting of hydrogen and alkyl having from 1 to 4 carbon atoms;
X is selected from the group consisting of alkylene, arylalkylene, and poly(alkyleneoxy), wherein alkylene and arylalkylene are each optionally interrupted by at least one functional group independently selected from the group consisting of ether, amine, ester, amide, carbamate, and urea;
Z is selected from the group consisting of an ammonium group, an amine-oxide group, an amine, a carboxylate, a sulfonate, a sulfate, phosphate, a phosphonate, and an amphoteric group, with the proviso that when X is alkylene having at least 10 carbon atoms, Z may also be hydrogen, and with the further proviso that when X is poly(alkyleneoxy), Z may also be selected from the group consisting of hydroxyl and alkoxy;
$Rf^a$ and $Rf^b$ independently represent a partially or fully fluorinated alkyl group having from 1 to 10 carbon atoms and optionally interrupted with at least one oxygen atom;
L is selected from the group consisting of F and $CF_3$;
W is selected from the group consisting of alkylene and arylene;
r is 0 or 1, wherein when r is 0, then $Rf^a$ is interrupted with at least one oxygen atom;
s is 1 or 2, wherein when s is 2, then Z is selected from the group consisting of an ammonium group, a phosphate, and a phosphonate;
t is 0 or 1;
m is 1, 2, or 3;
n is 0 or 1;
each p is independently a number from 1 to 6; and
z is a number from 2 to 7.

2. The compound according to claim 1, wherein Rf is selected from the group consisting of:
    $Rf^a—(O)_r—CHF—(CF_2)_n—$;
    $[Rf^b—(O)_t—C(L)H—CF_2—O]_m—W—$; and
    $CF_3CFH—O—(CF_2)_p—$.

3. The compound according to claim 1, wherein t and r are each 1, and wherein $Rf^a$ and $Rf^b$ are independently selected from the group consisting of:
    fully fluorinated aliphatic groups having from 1 to 6 carbon atoms; and
    fully fluorinated groups represented by formula:

$R_f^1—[OR_f^2]_x—[OR_f^3]_y—$, wherein
    $R_f^1$ is a perfluorinated aliphatic group having from 1 to 6 carbon atoms;
    $R_f^2$ and $R_f^3$ are each independently perfluorinated alkylene having from 1 to 4 carbon atoms; and
    x and y are each independently a number from 0 to 4, wherein the sum of x and y is at least 1.

4. The compound according to claim 1, wherein t and r are each 0, and wherein $R_f^a$ and $Rf^b$ are independently a fully fluorinated group represented by formula:

$R_f^4—[OR_f^5]_a—[OR_f^6]_b—O—CF_2—$, wherein
    $R_f^4$ is a perfluorinated aliphatic group having from 1 to 6 carbon atoms;
    $R_f^5$ and $R_f^6$ are each independently perfluorinated alkylene having from 1 to 4 carbon atoms; and
    a and b are each independently numbers from 0 to 4.

5. The compound according to claim 1, wherein Rf is selected from the group consisting of:
    $C_3F_7—O—CHF—$;
    $CF_3—O—CF_2CF_2—CF_2—O—CHF—$;
    $CF_3CF_2CF_2—O—CF_2CF_2—CF_2—O—CHF—$;
    $CF_3—O—CF_2—CF_2—O—CHF—$;
    $CF_3—O—CF_2—O—CF_2—CF_2—O—CHF—$;
    $CF_3—(O—CF_2)_2—O—CF_2—CF_2—O—CHF—$;
    $CF_3—(O—CF_2)_3—O—CF_2—CF_2—O—CHF—$;
    $CF_3—O—CHF—CF_2—$;
    $CF_3—O—CF_2—CF_2—O—CHF—CF_2—$;
    $CF_3—CF_2—O—CHF—CF_2—$;
    $CF_3—CF_2—CF_2—O—CHF—CF_2—$;
    $CF_3—O—CF_2—CF_2—CF_2—O—CHF—CF_2—$;
    $CF_3—O—CF_2—O—CF_2—CF_2—O—CHF—CF_2—$;
    $CF_3—(O—CF_2)_2—O—CF_2—CF_2—O—CHF—CF_2—$;
    $CF_3—(O—CF_2)_3—O—CF_2—CF_2—O—CHF—CF_2—$;
    $CF_3—O—CF_2—CHF—$;
    $C_3F_7—O—CF_2—CHF—$;
    $CF_3—O—CF_2—CF_2—CF_2—O—CF_2—CHF—$;
    $CF_3—O—CF_2—O—CF_2—CF_2—O—CF_2—CHF—$;
    $CF_3—(O—CF_2)_2—O—CF_2—CF_2—O—CF_2—CHF—$;
    $CF_3—(O—CF_2)_3—O—CF_2—CF_2—O—CF_2—CHF—$;
    $CF_3—O—CF_2—CHF—CF_2—$;
    $C_2F_5—O—CF_2—CHF—CF_2—$;
    $C_3F_7—O—CF_2—CHF—CF_2—$;

$CF_3$—O—$CF_2$—$CF_2$—$CF_2$—O—$CF_2$—CHF—$CF_2$—;
$CF_3$—O—$CF_2$—O—$CF_2$—$CF_2$—O—$CF_2$—CHF—$CF_2$—;
$CF_3$—(O—$CF_2$)$_2$—O—$CF_2$—$CF_2$—O—$CF_2$—CHF—$CF_2$—; and
$CF_3$—(O—$CF_2$)$_3$—O—$CF_2$—$CF_2$—O—$CF_2$—CHF—$CF_2$—.

6. The compound according to claim 5, wherein Rf is selected from the group consisting of $CF_3$—O—$CF_2CF_2$—$CF_2$—O—CHF—; $CF_3$—O—$CF_2$—$CF_2$—$CF_2$—O—$CF_2$—CHF—; $CF_3$—O—$CF_2$—$CF_2$—$CF_2$—O—CHF—$CF_2$—; and $CF_3$—O—$CF_2$—$CF_2$—$CF_2$—O—$CF_2$—CHF—$CF_2$—.

7. The compound according to claim 1, wherein Rf is $CF_3$—O—$(CF_2)_3$—O—$CF_2$—.

8. The compound according to claim 1, wherein Q is —C(O)—N(R')— or —C(O)O$^-$ $^+$NH(R')$_2$—.

9. The compound according to claim 1, wherein Q is –C(O)O$^-$ $^+$NH(R')$_2$—.

10. The compound according to claim 1, wherein Q is —C(O)—N(R')—, and wherein X is alkylene having up to 5 carbon atoms.

11. The compound according to claim 1, wherein Q is —C(O)O$^-$ $^+$NH(R')$_2$—, and wherein X is selected from the group consisting of alkylene having up to 5 carbon atoms, -[EO]$_f$—[R$^2$O]$_g$-[EO]$_f$—, and —[R$^2$O]$_g$-[EO]$_f$—[R$^2$O]$_g$—, wherein
EO represents —$CH_2CH_2O$—;
each R$^2$O independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O—;
each f is independently a number from 1 to 150; and
each g is independently a number from 0 to 55.

12. The compound according to claim 11, wherein the compound is represented by a formula selected from the group consisting of
[Rf—C(O)O$^-$ $^+$NH(R')$_2$—X]$_2$—NH(R)$^+$RfC(O)O$^-$ and
Rf—C(O)O$^-$ $^+$NH(R')$_2$—X—NH(R)$_2$$^+$RfC(O)O$^-$, and wherein each R is independently selected from the group consisting of hydrogen and alkyl having from 1 to 6 carbon atoms.

13. The compound according to claim 1, wherein Z is selected from the group consisting of —[N(R)$_3$]$^{30}$M$^{31}$, —N(O)(R$^1$)$_2$, —N$^+$(R)$_2$—X$^1$—SO$_3$A, and —N$^+$(R)$_2$—X$^1$—CO$_2$A, wherein
each R is independently selected from the group consisting of hydrogen and alkyl having from 1 to 6 carbon atoms;
each R$^1$ is independently selected from the group consisting of hydrogen and alkyl having from 1 to 6 carbon atoms, wherein alkyl is optionally substituted by at least one halogen, alkoxy, nitro, or nitrile group, or two R$^1$ groups may join to form a 5 to 7-membered ring optionally containing at least one O, N, or S and optionally substituted by alkyl having 1 to 6 carbon atoms;
each X$^1$ is selected from the group consisting of alkylene and arylalkylene, wherein alkylene and arylalkylene are each optionally interrupted by at least one ether linkage;
M$^-$ is a counter anion; and
A is selected from the group consisting of hydrogen and a free anion.

14. The compound according to claim 1, wherein Z is selected from the group consisting of —P(O)(OY)$_2$, —O—P(O)(OY)$_2$, —SO$_3$Y, —O—SO$_3$Y, and —CO$_2$Y, and wherein Y is selected from the group consisting of hydrogen and a counter cation.

15. The compound according to claim 1, wherein X-Z is selected from the group consisting of:
-[EO]$_f$—[R$^2$O]$_g$-[EO]$_f$—R$^3$; and
—[R$^2$O]$_g$-[EO]$_f$—[R$^2$O]$_g$—R$^3$,
wherein
EO represents —CH$_2$CH$_2$O—;
each R$^2$O independently represents —CH(CH$_3$)CH$_2$O—, —CH$_2$CH(CH$_3$)O—, —CH(CH$_2$CH$_3$)CH$_2$O—, —CH$_2$CH(CH$_2$CH$_3$)O—, or —CH$_2$C(CH$_3$)$_2$O—;
R$^3$ is hydrogen or alkyl having up to 4 carbon atoms;
each f is independently a number from 1 to 150; and
each g is independently a number from 0 to 55.

16. A method of reducing the surface tension of a liquid, the method comprising combining at least the liquid with an amount of the compound according to claim 1 sufficient to reduce the surface tension of the liquid.

* * * * *